US011155599B2

(12) United States Patent
Fueyo-Margareto et al.

(10) Patent No.: US 11,155,599 B2
(45) Date of Patent: Oct. 26, 2021

(54) ADENOVIRUSES EXPRESSING HETEROLOGOUS TUMOR-ASSOCIATED ANTIGENS

(71) Applicant: Board of Regents, The University of Texas System, Austin, TX (US)

(72) Inventors: Juan Fueyo-Margareto, Houston, TX (US); Candelaria Gomez-Manzano, Houston, TX (US); W. K. Alfred Yung, Houston, TX (US); Victor Krasnykh, Missouri City, TX (US); Hong Jiang, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/375,842

(22) PCT Filed: Feb. 1, 2013

(86) PCT No.: PCT/US2013/024506
§ 371 (c)(1),
(2) Date: Jul. 31, 2014

(87) PCT Pub. No.: WO2013/116778
PCT Pub. Date: Aug. 8, 2013

(65) Prior Publication Data
US 2014/0377294 A1    Dec. 25, 2014

Related U.S. Application Data

(60) Provisional application No. 61/594,005, filed on Feb. 2, 2012.

(51) Int. Cl.
*C12N 7/00* (2006.01)
*C07K 14/705* (2006.01)
*C07K 14/47* (2006.01)
*A61K 39/00* (2006.01)

(52) U.S. Cl.
CPC .. *C07K 14/70596* (2013.01); *A61K 39/00115* (2018.08); *A61K 39/00117* (2018.08); *A61K 39/001104* (2018.08); *A61K 39/001106* (2018.08); *A61K 39/001114* (2018.08); *A61K 39/001119* (2018.08); *A61K 39/001122* (2018.08); *A61K 39/001149* (2018.08); *A61K 39/001151* (2018.08); *A61K 39/001153* (2018.08); *A61K 39/001156* (2018.08); *A61K 39/001164* (2018.08); *A61K 39/001166* (2018.08); *A61K 39/001171* (2018.08); *A61K 39/001176* (2018.08); *A61K 39/001182* (2018.08); *A61K 39/001184* (2018.08); *A61K 39/001186* (2018.08); *A61K 39/001188* (2018.08); *A61K 39/001191* (2018.08); *A61K 39/001192* (2018.08); *A61K 39/001193* (2018.08); *A61K 39/001194* (2018.08); *A61K 39/001195* (2018.08); *C07K 14/4748* (2013.01); *C12N 7/00* (2013.01); *A61K 39/0011* (2013.01); *A61K 2039/5256* (2013.01); *C12N 2710/10034* (2013.01); *C12N 2710/10343* (2013.01)

(58) Field of Classification Search
CPC ........................................................ C12N 7/00
See application file for complete search history.

(56) References Cited

U.S. PATENT DOCUMENTS

| | | |
|---|---|---|
| 5,677,178 A | 10/1997 | McCormick |
| 5,801,029 A | 9/1998 | McCormick |
| 5,846,782 A | 12/1998 | Wickham et al. |
| 5,856,181 A | 1/1999 | McCormick |
| 6,080,578 A | 6/2000 | Bischoff et al. |
| 6,096,718 A | 8/2000 | Weitzman et al. |
| 6,403,370 B1 | 6/2002 | Alemany et al. |
| 6,455,498 B1 | 9/2002 | Vogelstein |
| 6,740,525 B2 | 5/2004 | Roelvink et al. |
| 6,756,044 B1 | 6/2004 | Roelvink et al. |
| 6,824,771 B1 | 11/2004 | Curiel et al. |
| 8,168,168 B2 | 5/2012 | Fueyo et al. |
| 2003/0138405 A1 | 7/2003 | Fueyo et al. |
| 2004/0175362 A1 | 9/2004 | Curiel et al. |
| 2006/0147420 A1 | 7/2006 | Fueyo et al. |
| 2007/0141028 A1 | 6/2007 | Hamada et al. |
| 2009/0155282 A1 | 6/2009 | Weber et al. |
| 2012/0207711 A1 | 8/2012 | Fueyo et al. |
| 2014/0227226 A1 | 8/2014 | Fueyo-Margareto et al. |
| 2014/0377221 A1 | 12/2014 | Fueyo-Margareto et al. |

FOREIGN PATENT DOCUMENTS

| | | |
|---|---|---|
| CN | 101607985 | 12/2009 |
| EP | 2383577 | 11/2011 |
| EP | 2407177 | 1/2012 |

(Continued)

OTHER PUBLICATIONS

Cascallo et al. (2007, Molecular Therapy, vol. 15(9), pp. 1607-1615).*
Piao et al. (2009, Cancer Gene Therapy, vol. 16(3), pp. 256-265).*
Garcia-Moure et al. (2017, J. Bone Oncology, vol. 9, pp. 41-47) (Year: 2017).*
Jiang et al. (2005, Neoplasia, vol. 7(1), pp. 48-56) (Year: 2005).*
Toth et al. (2010, Cancer Gene Ther., vol. 17(11), pp. 761-770) (Year: 2010).*
Alonso et al., "Adenovirus-based strategies overcome temozolomide resistance by silencing the O6-methylguanine-DNA methyltransferase promoter ," *Cancer Res*, 67(24): 11499-504, 2007.

(Continued)

*Primary Examiner* — Thaian N. Ton
*Assistant Examiner* — David A Montanari
(74) *Attorney, Agent, or Firm* — Parker Highlander PLLC

(57) ABSTRACT

The present invention is directed to adenoviruses for use in cancer therapy which comprise one or more heterologous nucleic acid sequences encoding a tumor antigen, whereby the adenovirus expresses the tumor antigen(s) on its surface.

17 Claims, 6 Drawing Sheets

Specification includes a Sequence Listing.

(56) References Cited

FOREIGN PATENT DOCUMENTS

| WO | WO 96/17053 | 6/1996 | |
|---|---|---|---|
| WO | WO 96/34969 | 11/1996 | |
| WO | WO 98/39467 | 9/1998 | |
| WO | WO 00/29599 | 5/2000 | |
| WO | WO 00/56909 | 9/2000 | |
| WO | WO 00/67576 | 11/2000 | |
| WO | WO 01/23004 | 4/2001 | |
| WO | WO 01/28569 | 4/2001 | |
| WO | WO 2003/087319 A1 * | 10/2003 | |
| WO | WO 2005/086922 | 3/2005 | |
| WO | WO 2009/117656 A2 * | 9/2009 | C12N 15/861 |
| WO | WO 2009/1117656 | 9/2009 | |
| WO | WO 2010/135242 | 11/2010 | |
| WO | WO 2011/134670 | 11/2011 | |
| WO | WO 2011/140284 | 11/2011 | |
| WO | WO 2013/076374 | 5/2013 | |
| WO | WO 2013/112942 | 8/2013 | |
| WO | WO 2014/204814 | 12/2014 | |

OTHER PUBLICATIONS

Hedley et al. (2006) Targeted and Shielded Adenovectors for Cancer Therapy. Cancer Immunol. Immunother. 55, 1412-1419.
Hedley et al. (2009) Assessment of genetic shielding for adenovirus vectors. Open Gene Therapy J., 2, 1-11.
Kaliberov, S. A., L. N. Kaliberova, et al. (2013). "Retargeting of gene expression using endothelium specific hexon modified adenoviral vector." Virology 447(1-2): 312-25.
Kurihara et al. (2000). Selectivity of a replication-competent adenovirus for human breast carcinoma cells expressing the MUC1 antigen. J. Clin. Invest., 106(6), 763-771.
Mathis et al. (2011) Genetic incorporation of human metallothionein into the adenovirus protein IX for non-invasive SPECT imaging. PLOS One. 6(2), e16792.
Office Communication issued in European Application No. 13706770.8, dated Nov. 28, 2016.
Office Communication issued in New Zealand Application No. 627736, dated Aug. 26, 2016.
Worgall et al. (2004). Modification to the capsid of the adenovirus vector that enhances dendritic cell infection and transgene-specific cellular immune responses. J Virol, 78(5), 2572-2580.
Worgall et al. (2005). Protection against P. aeruginosa with an adenovirus vector containing an OprF epitope in the capsid. J Clin Invest, 115(5), 1281-1289.
Wu, H., T. Han, et al. (2005). "Identification of sites in adenovirus hexon for foreign peptide incorporation." J Virol 79(6): 3382-90.
Adachi Y, et al., "A midkine promoter-based conditionally replicative adenovirus for treatment of pediatric solid tumors and bonennarrowtumoipurging," Cancer Res., 61(21): 7882-8, 2001.
Alemany et al., "CAR-binding ablation does not change biodistribution and toxicity of adenovirus vectors," Gene Therapy, 8: 1347-1353, 2001.
Alemany, R., et al., "Gene Therapy for Gliomas: Molecular Targets, Adenoviral Vectors, and Oncolytic Adenoviruses," Exp. Cell. Res., 252: 1-12, 1999.
Alemany, R., et al., "Growth inhibitory effect of anti-K-ras adenovirus on lung cancer cells," Cancer Gene Therapy, 3(5): 296-301, 1996.
Alonso et al., "Delta-24-RGD in combination with RAD001 induces enhanced anti-glioma effect via autophagic cell death", Molecular Therapy, 16(3): 487-493, 2008.
Alonso, "Can oncolytic adenovirus be implemented as therapeutic strategies for DIPGs?", DIPG European Meeting Barcelona, Feb. 2012.
Amalfitano, A., et al., "Improved adenovirus packaging cell lines to support the growth of replication-defective gene-delivery vectors," Proc Natl Acad Sci USA, 93: 3352-6, 1996.
Anderson et al., "Plasmid DNA and viral vector-based vaccines for the treatment of cancer", Vaccine, 25S: B24-B34, 2007.
Anderson, W.F., "Human Gene Therapy," Nature, 392: 25-30, 1998.
Arap, W., et al., "Cancer Treatment by Targeted Drug Delivery to Tumor Vasculature in a Mouse Model," Science, 279: 377-80, 1998.
Babiss et al., "Cellular Promoters Incorporated into the Adenovirus Genome," J. Mol. Biol., 193: 643-650, 1987.
Bangma et al., "Free Serum Prostate-Specific Antigen and Screening for Prostate Cancer," JAMA, 275(11 ): 837-8, 1996.
Barnes, et al., "Conditionally Replicative Adenoviruses for Ovarian Cancer Therapy", Mol. Cancer Thera., 1:435-439, 2002.
Beck et al., "The Thymidine Kinase/Ganciclovir-Mediated "Suicide" Effect Is Variabkle in Different Tumor Cells", Human Gene Therapy, 6: 1525-1530, 1995.
Bergelson, J.M., et al., "Isolation of a Common Receptor for Coxsackie B Viruses and Adenoviruses 2 and 5," Science, 275: 1320-3, 1997.
Bien et al., "Pre-treatment serum levels of interleukin-10, interleukin-12 and their ratio predict response to therapy and probability of event-free and overall survival in childhood soft tissue sarcomas, Hodgkin's lymphomas and acute lymphoblastic leukemias", Clinical Biochemistry, 42(10-11): 1144-1157, 2009.
Bischoff, J. R., et al., "An Adenovirus Mutant That Replicates Selectively in p53-Deficient Human Tumor Cells," Science, 274:373-376, 1996.
Blackwell, J., et al., "Retargeting to EGFR Enhances Adenovirus Infection Efficiency of Squamous Cell Carcinoma," Arch. Otolaryngol. Head Neck Surg., 125: 856-863, 1999.
Bonetta et al., "Research Notes", Nature Genetics, 34(2): 133, 2003.
Carbone, F.R., et al., "Cross-presentation: A General Mechanism for CTL Immunity and Tolerance," Immunol. Today, 19(8): 368-73, 1998.
Chartier, C., et al., "Efficient Generation of Recombinant Adenovirus Vectors by Homologous Recombination in Escherichia coli," J. Virol., 70(7): 4805-10, 1996.
Chiocca, "Oncolytic viruses", Nat Rev Cancer, 2(12): 938-50, 2002.
Cook, D.R., et al., "Gene Therapy for B-cell Lymphoma in a SCID Mouse Model using an Immunoglobulin-Regulated Diphtheria Toxin Gene Delivered by a Novel Adenovirus-Polylysine Conjugate," Cancer Biother., 9(2): p. 131-141, 1994.
Curiel, "Strategies to Adapt Adenoviral Vectors for Targeted Delivery," Annals New York Academy of Sciences, 886: 158-171, 1999.
Curia D.T., "Strategies to improve the therapeutic utility of conditionally replicative adenoviruses (CRAds) for cancer therapy," Proc. Amer. Assoc. Cancer Res. Ann. Meet. 43: 662-663, abstract 3287, Mar. 2002.
Dachs et al., "Targeting gene therapy to cancer: A Review," Oncology Res., 9: 313-325, 1997.
Database Accession No. AYD24277, dated Aug. 19, 2010.
Database Accession No. AYD74276, dated Aug. 19, 2010.
Deng, Y., et al., "MHC Affinity, Peptide Liberation, T Cell Repertoire, and Immunodominance All Contribute to the Paucity of MHC Class I-Restricted Peptides Recognized by Antiviral CTL," J. Immunol., 158: 1507-15, 1997.
Dion, L.D., et al., "E1A RNA transcripts amplify adenovirus-mediated tumor reduction," Gene Therapy, 3: 1021-5, 1996.
Dion, L.D., et al., "Quantitative and in vivo activity of adenoviral-producing cells made by cotransduction of a replication-defective adenovirus and a replication-enabling plasmid," Cancer Gene Therapy, 3( 4): 230-7, 1996.
Dmitriev, I., et al., "An Adenovirus Vector with Genetically Modified Fibers Demonstrates Expanded Tropism via Utilization of a Coxsackievirus and Adenovirus Receptor-Independent Cell Entry Mechanism," J. Virol., 72(12): 9706-13, 1998.
Dobner, T., et al., "Blockage by Adenovirus E4orf6 of Transcriptional Activation by the p53 Tumor Suppressor," Science, 272: 1470-3, 1996.
Eck et al., "Gene-based therapy," Goodman & Oilman's The Pharmacological Basis of Therapeutics, 9th Ed., McGraw-Hill, 1996. 77-101. Print.
Eustace, D., et al., "Interleukin-6 (IL-6) Functions as an Autocrine Growth Factor in Cervical Carcinomas in Vitro," Gynecol. Oncol., 50: 15-19, 1993.

(56) References Cited

OTHER PUBLICATIONS

Fallaux, F.J., et al., "New Helper Cells and Matched Early Region I-Deleted Adenovirus Vectors Prevent Generation of Replication-Competent Adenoviruses," *Human Gene Therapy*, 9: 1909-17, 1998.
Fechner, H., et al., "Expression of Coxsackie adenovirus receptor and alphav-integrin does not correlate with adenovector targeting in vivo indicating anatomical vector barriers," *Gene Therapy*, 6: 1520-1535, 1999.
Ferguson et al., "Systemic delivery of oncolytic viruses: hopes and hurdles", *Advances in Virology*, 2012: 805629, 2012.
Ferrin, L.J., "Manipulating and Mapping DNA with RecA-Assisted Restriction Endonuclease (RARE) Cleavage," *Genet. Eng.*, 17: 21-30, 1995.
Fick et al., "The extent of heterocellular communication mediated by gap junctions is predictive of bystander tumor cytotoxicity in vitro", *Proc. Natl. Acad. Sci.*, 92: 11071-11075, 1995.
Forsythe JA, et al., "Activation of vascular endothelial growth factor gene transcription by hypoxia-inducible factor 1," *MolCell Biol.*, 16(9):4604-13, 1996.
Fox, "Investigation of gene therapy begins", *Nature Biotechnology*, 18: 143-144, 2000.
Freytag et al., "A Novel Three-Pronged Approach to Kill Cancer Cells Selectively: Concomitant Viral, Double Suicide Gene, and Radiotherapy", *Human Gene Ther.*, 9: 1323-1333, 1998.
Fueyo et al., "Preclinical characterization of the antiglioma activity of a tropism-enhanced adenovirus targeted to the retinoblastoma pathway", *Journal of National Cancer Institute*, 95(9): 652-60, 2003.
Fueyo, J., et al., "A mutant oncolytic adenovirus targeting the Rb pathway produces anti-glioma effect in vivo," *Oncogene*, 19: 2-12, 2000.
Garver R., Jr., et al., "Strategy for achieving selective killing of carcinomas," *Gene Therapy*, 1: 46-50, 1994.
Goldman, C.K, et al., "Targeted Gene Delivery to Kaposi's Sarcoma Cells via the Fibroblast Growth Factor Receptor," *Cancer Res.*, 57: 1447-51, 1997.
Goldsmith, K.T., et al., "trans E1 Component Requirements for Maximal Replication of E1-Defective Recombinant Adenovirus," *Virology*, 248: 406-19, 1998.
Goldsmith, K.T., et al., "Trans Complementation of an E1A-Deleted Adenovirus with Codelivered E1A sequences to Make Recombinant Adenoviral Producer Cells," *Human Gene Therapy*, 5: 1341-8, 1994.
Gomez-Manzano, C., et al., "Adenovirus-mediated Transfer of the p53 Gene Produces Rapid and Generalized Death of Human Glioma Cells via Apoptosis," *Cancer Res.*, 56: 694-9, 1996.
Goodrum, F.D., et al., "p53 Status Does Not Determine Outcome of E1B 55-Kilodalton Mutant Adenovirus Lytic Infection," *J. Virol.*, 72(12): 9479-90, 1998.
Gotoh, A., et al., "Development of Prostate-Specific Antigen Promoter-Based Gene Therapy for Androgen-Independent Human Prostate Cancer," *J. Urol.*, 160: 220-9, 1998.
Green and Seymour, "Adenoviral vectors: systemic delivery and tumor targeting", *Cancer Gene Therapy*, 9: 1036-1042, 2002.
Hall, A.R., et al., "p53-dependent cell death/apoptosis is required for a productive adenovirus infection," *Nat. Med.*, 4(9): 1068-72, 1998.
Hardy, S., et al, "Construction of Adenovirus Vectors through Cre-lox Recombination," *J. Virol.*, 71(3): 1842-1849, 1997.
He et al., "A simplified system for generating recombinant adenoviruses," *Proc Natl Acad Sci U S A.*, 95(5): 2509-14, 1998.
Hearing and Shenk, "Sequence-independent autoregulation of the adenovirus type 5 E1A transcription unit", *Molecular and Cellular Biology*, 5(11):3214-3221, 1985.
Heise et al., "An adenovirus E1A mutant that demonstrates potent and selective systemic anti-tumoral efficacy," *Nature Medicine*, 6(10):1134-1139, 2000.

Heise, C., et al., "ONYX-015, an E1B gene-attenuated adenovirus, causes tumor-specific cytolysis and antitumoral efficacy that can be augmented by standard chemotherapeutic agents," *Nat. Med.*, 3: 639-645, 1997.
Heise, C.C., et al., "Efficacy of a replication-competent adenovirus (ONYX-015) following intratumoral injection: Intratumoral spread and distribution effects," *Cancer Gene Therapy*, 6: 499-504, 1996.
Hemmi, S., et al., "The Presence of Human Coxsackievirus and Adenovirus Receptor Is Associated with Efficient Adenovirus-Mediated Transgene Expression in Human Melanoma Cell Cultures," *Human Gene Therapy*, 9: 2363-73, 1998.
Hemminki and Johansson, "Cancer gene therapy in humans", Cancer Gene Therapy Group—University of Helsinki, dated Apr. 6, 2011.
Hemminki et al., "Serotype chimeric oncolytic adenovirus Ad5/3-Δ24 for targeted virotherapy of ovarian cancer", RAID application dated Aug. 2003.
Hobbs et al., "Regulation If transport pathways in tumor vessels: Role of tumor type and microenvironment", *Proc. Natl. Acad. Sci.*, 95: 4607-4612, 1998.
Hofmann, C., et al., "Ovine Adenovirus Vectors Overcome Preexisting Humoral Immunity against Human Adenoviruses in Vivo," *J. Virol.*, 73: 6930-36, 1999.
Tinier et al., "Novel complementation cell lines derived from human lung carcinoma A549 cells support the growth of E1-deleted adenovirus vectors," *Gene Ther.* 3: 75-84, 1996.
Jain, "Delivery of Molecular and Cellular Medicine to Solid Tumors", *Journal of Controlled Release*, 53: 49-67, 1998.
Jiang et al., "Examination of the therapeutic potential of delta-24-RGD in brain tumor stem cells: role of autophagic cell death", *Journal of the National Cancer Institute* (GB), 99(18): 1410-1414, 2007.
Jiang et al., "Oncolytic adenovirus: preclinical and clinical studies in patients with human malignant gliomas", *Curr Gene Ther.*, 9(5):422-427, 2009.
Kasono, K., et al., "Selective Gene Delivery to Head and Neck Cancer Cells via an Integrin Targeted Adenoviral Vector," *Clin. Cancer Res.*, 5: 2571-2579, 1999.
Kim, D., et al., "ONYX-015: Clinical data are encouraging," *Nat. Med.*, 4(12): 1341-2, 1998.
Kim, D., et al., "Replicating Viruses as Selective Cancer Therapeutics," *Mol. Med. Today*, 2(12): 519-27, 1996.
Koivunen, E., et al., "Identification of Receptor Ligands with Phage Display Peptide Libraries," *J. Nucl. Med.*, 40: 883-888, 1999.
Kong, B., et al., "IL-6 Antisense-Mediated Growth Inhibition of a Choriocarcinoma Cell Line: An Intracellular Autocrine Growth Mechanism," *Gynecol. Oncol.*, 63: 78-84, 1996.
Krasnykh, V., et al., "Characterization of an Adenovirus Vector Containing a Heterologous Peptide Epitope in the HI Loop of the Fiber Knob," *J. Virol.*, 72(3): 1844-52, 1998.
Krasnykh, V., et al., "Generation of Recombinant Adenovirus Vectors with Modified Fibers for Altering Viral Tropism," *J. Virol.*, 70: 6839-6846, 1996.
Krause et al., "Epitopes expressed in different adenovirus capsid proteins induce different levels of epitope-specific immunity", *Journal of Virology*, 80(11): 5523-5530, 2006.
Kremer, E. J., et al., "Canine Adenovirus Vectors: an Alternative for Adenovirus-Mediated Gene Transfer," *J. Virol.*, 74: 505-512, 2000.
Laquerre et al., "Recombinant Herpes Simplex Virus Type 1 Engineered for Targeted Binding to Erythropoietin Receptor-Bearing Cells," *Journal of Virology*, 72(12): 9683-9697, 1998.
Lee et al., "Enhanced antitumor effect of oncolytic adenovirus expressing interleukin-12 and B7-1 in an immunocompetent murine model", *Clinical Cancer Research*, 12:5859-5868, 2006.
Leissner et al., "Influence of adenoviral fiber mutations on viral encapsidation, infectivity and in vivo tropism," Gene Therapy 8: 49-57, 2001.
Majem et al., "Control of E1A under an E2F-1 promoter insulated with the myotonic dystrophy locus insulator reduces the toxicity of oncolytic adenovirus Ad-Δ24RGD," *Cancer Gene Therapy*, 13:696-705, 2006.
Miller, C.R., et al., "Differential Susceptibility of Primary and Established Human Glioma Cells to Adenovirus Infection: Target-

(56) References Cited

OTHER PUBLICATIONS ing via the Epidermal Growth Factor Receptor Achieves Fiber Receptor-independent Gene Transfer," *Cancer Res.*, 58: 5738-48, 1998.
Miller, N., et al., "Progress in Transcriptionally Targeted and Regulatable Vectors for Genetic Therapy," *Human Gene Therapy*, 8: 803-15, 1997.
Mittereder, N., et al., "Evaluation of the Concentration and Bioactivity of Adenovirus Vectors for Gene Therapy," *J. Virology*, 70(11):7498-509, 1996.
Mocellin et al., "Kinetics of cytokine expression in melanoma metastases classifies immune responsiveness", *Int J Cancer*, 93: 236-242, 2001.
Moolten, F. L., "Drug Sensitivity ("suicide") genes for selective cancer chemotherapy," *Cancer Gene Therapy*, 1(4): 279-87, 1994.
Moran, E., "Interaction of adenoviral proteins with pRB and p53," *Faseb J*, 7: 880-5, 1993.
Murray, E.J., et al., "Sequences and Factors Required for the F9 Embryonic Carcinoma Stem Cell E1a-Like Activity," *Mol. Cell Biol.*, 11(11): 5534-40, 1991.
NCBI Reference Sequence: GenBank Accession No. AC _000008.1, Dec. 1, 2004.
Nelson, J.E., et al., "Persistence of Recombinant Adenovirus In Vivo Is Not Dependent on Vector DNA Replication," *J. Virol.*, 71(11): 8902-7, 1997.
Nokisalmi et al., "Oncolytic adenovirus ICOVIR-7 in patients with advanced and refractory solid tumors", *Clinical Cancer Research*, 16(11):3035-3043, 2010.
Office Communication issued in Chinese Application No. 201380010639.1, dated Sep. 6, 2015. (English Translation).
Office Communication issued in New Zealand Application No. 627736, dated Mar. 31, 2015.
Office Communication issued in Chinese Application No. 201380017639.4, dated Sep. 15, 2015. (English Translation).
Office Communication issued in European Application No. 13704334.5, dated Mar. 2, 2016.
Office Communication issued in New Zealand Application No. 628213, dated Apr. 24, 2015.
Ohta Y, et al., "Significance of vascular endothelial growth factor messenger RNA expression in primary lung cancer," *ClinCancer Res.*, 2(8): 1411-6, 1996.
O'Riordan, C., et al., "PEGylation of Adenovirus with Retention of Infectivity and Protection from Neutralizing Antibody in Vitro and in Vivo," *Human Gene Therapy*, 10: 1349-1358, 1999.
Paillard, F., "The Search for the "Best" Cytokine to Induce Anti-tumor Immunity," *Hum Gene Therapy*, 9: 2457-8, 1998.
Pasqualini, R., et al., "αv Integrins as receptors for tumor targeting by circulating ligands," *Nat. Biotechnol.*, 15: 542-6, 1997.
PCT International Preliminary Report on Patentability issued in International Application No. PCT/US2013/024506, dated Aug. 14, 2014.
PCT International Preliminary Report on Patentability issued in International Application No. PCT/US2013/023304, dated Aug. 7, 2014.
PCT International Search Report and Written Opinion issued in International Application No. PCT/US2013/023304, dated Apr. 11, 2013.
PCT International Search Report and Written Opinion issued in International Application No. PCT/US2013/024506, dated Oct. 28, 2013.
PCT International Search Report and Written Opinion issued in International Application No. PCT/US2014/042375, dated Oct. 7, 2014.
PCT Invitation to Pay Additional Fees issued in International Application No. PCT/US2013/023304, dated Apr. 19, 2013.
Peng et al., "Viral vector targeting," *Current Opinion in Biotechnology*, 10: 454-457, 1999.

Raben, D., et al., "Enhancement of radiolabeled antibody binding and tumor localization through adenoviral transduction of the human carcinoembryonic antigen gene," *Gene Therapy*, 3: 567-80, 1996.
Rajotte, "Molecular Heterogeneity of the Vascular Endothelium Revealed by in Vivo Phage Display," *J. Clin. Invest.*, 102: 430-437, 1998.
Rancourt et al., "Conditionally replicative adenoviruses for cancer therapy", *Advanced Drug Delivery Reviews*, 27: 67-81, 1997.
Rasmussen, et al., "Matrix Metalloproteinase Inhibition as a Novel Anticancer Strategy: A Review with Special Focus on Batimastat and Marimastat," *Pharmacol Ther.*, 75(1): 69-75, 1997.
Reid et al., "Intravascular adenoviral agents in cancer patients: lessons from clinical trials", *Cancer Gene Therapy*, 9: 979-986, 2002.
Rodriguez, R., et al., "Prostate Attenuated Replication Competent Adenovirus (ARCA) CN706: A Selective Cytotoxic for Prostate-specific Antigen-positive Prostate Cancer Cells," *Cancer Res.*, 57(13): 2559-63, 1997.
Roelvink et al., "The coxsachievirus-adenovirus receptor protein can function as a cellular attachment protein for adenovirus serotypes from subgroups A, C, D, E, and F," *J. Virol.*, 72(10): 7909-7915, 1998.
Roelvink, P. W., et al., "Identification of a Conserved Receptor-Binding Site on the Fiber Proteins of CAR-Recognizing Adenoviridae," *Science*, 286: 1568-1571, 1999.
Roklilin, O.W., et al., "Expression of Cellular Adhesion Molecules on Human Prostate Tumor Cell Lines," *Prostate*, 26: 205-212, 1995.
Roth, J., et al., "Gene Therapy for Cancer: What Have We Done and Where Are We Going?," *J. Natl Cancer Inst.*, 89(1): 21-39, 1997.
Rothmann, T., et al., "Replication of ONYX-015, a Potential Anticancer Adenovirus, Is Independent of p53 Status in Tumor Cells," *J. Virol.*, 72(12): 9470-8, 1998.
Rouslahti and Rajotte, "An address system in the vasculature of normal tissues and tumors", *Annu Rev Immunol.*, 18:813-27, 2000.
Russell, S.J. "Replicating vectors for cancer therapy: a question of strategy," *Semin. Cancer Biol.*, 5: 437-43, 1994.
Sandhu et al., "Human Gene Therapy," *Critical Reviews in Biotechnol.*, 17(4): 307-326, 1997.
Scaria, A., et al., "Complementation of a human adenovirus early region 4 deletion mutant in 293 cells using adenovirus polylysine-DNA complexes," *Gene Therapy*, 2: 295-8, 1995.
Schreiber H. "Tumor Immunology," *Fundamental Immunology*, 4th Ed., W.E. Paul, Editor. Lippincott-Raven Publishers: Philadelphia, 1999. 1237-1270. Print.
Schuepbach, J., et al., "Inverse Correlation of Antiviral Antibody Titers and the Remission Length in Patients Treated with Viral Oncolysate: A Possible New Prognostic Sign in Acute Myelogenous Leukemia," *Cancer*, 48: 1363-7, 1981.
Shi, Q., et al., "Modulation of the Specificity and Activity of a Cellular Promoter in an Adenoviral Vector," *Human Gene Therapy*, 8: 403-10, 1997.
Shinoura N. et al., "Highly augmented cytopathic effect of a fiber-mutant E1B-defective adenovirus for gene therapy of gliomas," *Cancer Res.*, 59(14): 3411-6, 1999.
Sinkovics, J., et al., "New Developments in the Virus Therapy of Cancer: A Historical Review," *Intervirology*, 36: 193-214, 1993.
Smith, C.A., et al.,"Adenovirus-Pulsed Dendritic Cells Stimulate Human Virus-Specific T-Cell Responses in Vitro," *J. Virology*, 70(10): 6733-40, 1996.
Spergel, J., et al., "Interleukin 6 enhances a cellular activity that functionally substitutes for E1A protein in transactivation," *Proc Natl Acad Sci USA*, 88: 6472-6, 1991.
Stevenson et al., "Selective Targeting of Human Cells by a Chimeric Adenovirus Vector Containing a Modified Fiber Protein", *Journal of Virology*, 71(6): 4782-4790, 1997.
Stevenson, S., et al., "Human Adenovirus Serotypes 3 and 5 Bind to Two Different Cellular Receptors via the Fiber Head Domain," *J. Virol.*, 69: 2850-2857, 1995.
Sussenbach, J, "The Structure of the Genome", *The Adenoviruses* (1984), Chapter 3, pp. 35-124.

(56) References Cited

OTHER PUBLICATIONS

Suzuki et al., "A conditionally replicative adenovirus with enhanced infectivity shows improved oncolytic potentcy", *Clinical Cancer Research*, 7: 120-126, 2001.
Tabora et al., "Emerging concepts in biomarker discovery; the US-Japan workshop on immunological molecular markers in oncology", *Journal of Translational Medicine*, 7(1): 45, 2009.
Takayama et al., "Conditionally replicative adenovirus, AdVEGFE1, has a possibility for universal application in various cancer treatments", *Mol. Ther.*, 5: S268, abstract 821, May 2002.
Takayama et al., "VEGF promoter-based conditionally replicative adenovirus are useful for the treatment of lung cancer," *Mol. Ther.* 7(5, Part 2): 5420, abstract 1089, 2003.
Takayama K, et al., "Suppression of tumor angiogenesis and growth by gene transfer of a soluble form of vascular endothelial growth factor receptor into a remote organ," *Cancer Res.*, 60(8):2169-77, 2000.
Takayama K, et al., "The levels of integrin alpha v beta 5 may predict the susceptibility to adenovirus-mediated gene transfer in human lung cancer cells," *Gene Ther.*, 5(3):361-8, 1998.
Takenawa, J., et al., "Enhanced Expression of interleukin-6 in Primary Human Renal Cell Carcinomas", *J Natl Cancer Inst*, 83(22): 1668-72, 1991.
Tanaka, T., et al., "Viral Vector-targeted Antiangiogenic Gene Therapy Utilizing an Angiostatin Complementary DNA," *Cancer Res.*, 58: 3362-9, 1998.
Todo, T., et al., "Systemic Antitumor Immunity in Experimental Brain Tumor Therapy Using a Multimutated, Replication-Competent herpes Simplex Virus," *Human Gene Therapy*, 10: 2741-2755, 1999.
Urban, J.L., et al., "Stepwise Immunologic Selection of Antigenic Variants During Tumor Growth," *J. Immunology*, 137(9): 3036-41, 1986.
Vanderkwaak et al.," Adenovirus with RGD-modified fiber demonstrates improved gene transfer into ovarian carcinoma cell lines and ovarian primary tumors" in Abstracts Presented for the thirtieth annual meeting of the society of gynecologic oncologists, *Gynecologic Oncology*, 72(3): 443-527, 1999. Abstract 254, p. 505.
Verma et al., "Gene therapy—promises, problems and prospects", *Nature*, 389: 239-242, 1997.
Vile et al., "The oncolytic virotherapy treatment platform for cancer: Unique biological and biosafety points to consider", *Cancer Gene Therapy*, 9:1062-1067, 2002.
Von Seggern et al., "Adenovirus Vector Pseudotyping in Fiber-Expressing Cell Lines: Improved Transduction of Epstein-Barr Virus-Transformed B Cells," *J. Virol.*, 74: 354-362, 2000.
Wen et al., "Tricistronic viral vectors co-expressing interleukin-12 (IL-12) and CD80 (B7-1) for the immunotherapy of cancer: preclinical studies in myeloma", *Cancer Gene Therapy*, 8(5): 361-370, 2001.
Whyte et al., "Cellular targets for transformation by the adenovirus E1A proteins," *Cell*, 56:67-75, 1989.
Whyte et al., "Two regions of the adenovirus early region 1A proteins are required for transformation," *Journal of Virology*, 62(1):257-265, 1988.
Wickham, T., et al., "Increased In Vitro and In Vivo Gene Transfer by Adenovirus Vectors Containing Chimeric Fiber Proteins," *J. Virol.*, 71(11): 8221-9, 1997.
Wildner, O., et al., "Adenoviral vectors capable of replication improve the efficacy of HSVtk/GCV suicide gene therapy of cancer," *Gene Therapy*, 6: 57-62, 1999.
Wildner, O., et al., "Therapy of Colon Cancer with Oncolytic Adenovirus Is Enhanced by the Addition of Herpes Simplex Virus-thymidine kinase," *Cancer Res.*, 59: 410-413, 1999.
Wittke et al., "Interleukin 10 (IL-10): an immunosuppressive factor and independent predictor in patients with metastatic renal cell carcinoma", *British Journal of Cancer*, 79(7/8): 1182-1184, 1999.

Wongthida et al., "Type III IFN interleukin-28 mediates the antitumor efficacy of oncolytic virus VSV in immune-competent mouse models of cancer", *Cancer Research*, 70(11): 4539-4549, 2010.
Worgall, S., et al., "Innate Immune Mechanisms Dominate Elimination of Adenoviral Vectors Following In Vivo Administration," *Human Gene Therapy*, 8: 37-44, 1997.
Worschech et al., "Systemic treatment of xenografts with vaccinia virus GLV-1h68 reveals the immunologic facet of oncolytic therapy", *BMC Genomics*, 10(1): 301, 2009.
Xia, et al., "Structure of the Receptor Binding Domain of Adenovirus Type 5 Fiber Protein," *Curr. Top. Microbiol. Immunol.*, 199 (1): 39-46, 1995.
Yang, Y., et al., "Recombinant IL-12 prevents formation of blocking IgA antibodies to recombinant adenovirus and allows repeated gene therapy to mouse lung," *Nat. Med.*, 1: 890-893, 1995.
Yeh, P., et al., "Advances in adenoviral vectors: from genetic engineering to their biology," *FASEB J*, 11: 615-23, 1997.
Yoshida, Y., et al., "Generation of Fiber-Mutant Recombinant Adenoviruses for Gene Therapy of Malignant Glioma," *Human Gene Therapy*, 9: 2503-15, 1998.
Yu, D. C., et al., "Identification of the Transcriptional Regulatory Sequences of Human Kallikrein 2 and Their Use in the Construction of Calydon Virus 764, an Attenuated Replication Competent Adenovirus for Prostate Cancer Therapy", *Cancer Res.*, 59: 1498-1504, 1999.
Yu D. et al., "Enhanced c-erbB-2/neu Expression in Human Ovarian Cancer Cells Correlates with More Severe Malignancy that can be Suppressed by E1A", *Cancer Res.*, 53: 891-8, 1993.
Yurkovetsky et al., "Multiplex analysis of serum cytokines in melanoma patients treated with interferon-2b", *Clinical Cancer Research*, 13(8): 2422-2428, 2007.
Zhang et al., "Eradication of solid human breast tumors in nude mice with an intravenously injected light-emitting oncolytic vaccinia virus", *Cancer Research*, 67(20): 10038-10046, 2007.
Zhang, J., et al., "Vectors for Cancer Gene Therapy," *Cancer Metastasis Rev.*, 15: 385-401, 1996.
Zheng, D. Q., et al., "Prostatic Carcinoma Cell Migration via alpha(v)beta3 Integrin is Modulated by a Focal Adhesion Kinase Pathway," *Cancer Res.*, 59: 1655-1664, 1999.
Jarnagin et al., "Neoadjuvant treatment of hepatic malignancy: an oncolytic herpes simplex virus expressing IL-12 effectively treats the parent tumor and protects against recurrence-after resection ," *Cancer Gene Therapy*, 10: 215-223, 2003.
Kim et al., "Enhanced antitumour immunity by combined use of temozolomide and TAT-survivin pulsed dendritic cells in a murine glioma" *Immunology*, 122: 615-622, 2007.
Office Communication issued in corresponding Chinese Application No. 201380010639.1, dated Jul. 5, 2016.
Cerullo et al. "Immunological effects of low-dose cyclophosphamide in cancer patients treated with oncolytic adenovirus", *Molecular Therapy*, 19(9): 1737-1746, 2011.
Dziurzynski et al. "Cytomegalovirus Subverts the Monocyte Lineage to Become Glioma. Propagating," *Neuro-Oncology*, 13: iii30-iii33, 2011.
Grauer et al. "CD4+FoxP3+ regulatory T cells gradually accumulate in gliomas during tumor growth and efficiently suppress antiglioma immune responses in vivo", *Int. J. Cancer*, 121: 95-105, 2007.
Murphy et al. "Janeway's Immunobiology", 7th ed. 2008. Japanese Translation of pp. 427-429.
Office Communication issued in corresponding Japanese Application No. 2014-554887, dated Dec. 26, 2016.
Office Communication issued in corresponding Chinese Application No. 201380010639.1, dated Jan. 16, 2017.
Szabo and Carpentier, "Immunotherapy in human glioblastoma", *Revue Neurologique*, 167(10): 668-672, 2011.
Office Communication issued in corresponding Chinese Application No. 2014-554887, dated Apr. 25, 2017.
Shi et al., "Recombinant adenovirus-mediated human wild type p53, GM-CSF, and B7-1 genes enhance the immunogenicity of primary liver cancer cells", Chinese Journal of Immunology, vol. 18, 769-771, 2002.

\* cited by examiner

A

B

ADENOVIRUSES EXPRESSING HETEROLOGOUS TUMOR-ASSOCIATED ANTIGENS

CROSS-REFERENCE TO RELATED APPLICATIONS

This application is a national phase application under 35 U.S.C. § 371 of International Application No. PCT/US2013/024506, filed Feb. 1, 2013, which claims the benefit of U.S. Provisional Application No. 61/594,005, filed Feb. 2, 2012, the entire content of each of which is specifically incorporated herein by reference.

BRIEF DESCRIPTION OF SEQUENCE LISTING, TABLES, AND COMPUTER PROGRAM LISTING

A sequence listing is attached to the present application in a file named SEQ.tx (4 KB, 1 Feb. 2013), and is hereby incorporated by reference herein.

BACKGROUND

I. Field of Invention

The present invention relates generally to the fields of oncology and cancer therapy. More particularly, it concerns immunogenic adenovirus.

II. Description of Related Art

Cancer remains one of the leading causes of morbidity and mortality in humans worldwide. Although surgery, chemotherapy and radiation have been utilized with some success to cure cancer, novel strategies are needed. Viruses that replicate in tumor cells better than in normal cells have shown promise as oncolytic agents. The feasibility of gene transfer and tumor lysis using adenoviruses has been well established (Kirn, 1999; Bischoff et al., 1996; Wildner et al., 1999a; Wildner et al., 1999b; (Sterman et al., Hum. Gene Ther. 9: 1083-1092 (1998)).

There remains a need for additional anti-cancer therapies.

SUMMARY

There are at least four mechanisms by which replication competent adenovirus can effect anti-cancer therapy. First, adenovirus can initiate and complete a lytic infection, thereby lysing the cells (oncolysis). Second, adenovirus can express suicide genes, such as thymidine kinase (HSVtk) gene or the cytosine deaminase-thymidine kinase fusion protein (Rogulski et al., Clin. Cancer Res. 3: 2081-2088 (1997)), which will augment the oncolytic activity. Third, administration of adenovirus can be combined with chemotherapy (including any drug therapy), or radiation to enhance the oncolytic activity of each agent (Nielsen et al., Cancer Gene Ther. 4: 835-846 (1997)). Finally, the virus could function as an immunostimulant, or as a vector that expresses immunstimulatory molecules, resulting in the stimulation of specific immune effector cells against tumor antigens. A combination strategy using oncolysis and immune stimulation is particularly appealing because it may offer a long-term, durable response through a "vaccine effect." Thus, until the present invention, there has remained a need in the art for a replication selective adenovirus having improved selectively for tumor cells expressing or displaying tumor associated antigens.

The present invention relates to adenovirus compositions having cancer antigens incorporated into adenovirus coat proteins, cancer antigens expressed by the adenovirus, or cancer antigens delivered with an adenovirus. In certain aspects, modified coat proteins will comprise modified fiber proteins, hexon proteins, or pIX proteins. An antigen-modified adenovirus will present cancer antigens from the first replication cycle, elevating the level of cancer antigens in the tumor milieu. The elevated level of antigens in the tumor milieu will stimulate an immune response against the cancer antigens and against lysed tumor cells. In certain aspects, the stimulation of the immune response in combination with the lysis of the tumor cells provides an enhanced anti-tumor immunity that increases the probability of tumor regression.

A chimeric adenovirus coat protein can comprise from about 3, 4, 5, 6, 7, 8, 9, 10, 11, 12, 13, 14, 15, 16, 17, 18, 19, 20, 21, 22, 23, 24, 25, 26, 27, 28, 29 to about 30 heterologous amino acids inserted into or in place of coat protein amino acid sequence, or, alternatively, fused to the C-terminus of an adenovirus coat protein. The adenovirus coat protein can be a fiber protein, a penton base protein, a hexon, or a pIX protein. An antigen can be inserted in the hexon hypervariable region 1 (human adenovirus type 5 amino acids 139-167), fiber protein HI loop (human 5 adenovirus type 5 fiber HI loop amino acids 537-549), and/or conjugated or fused to protein IX (human adenovirus type 5 protein IX amino acid 140). In certain aspects the heterologous amino acids are linked to the chimeric adenovirus coat protein by a spacer sequence of from about 3 amino acids to about 30 amino acids, including all values and ranges there between.

Thus, embodiments include an adenovirus having multiple tumor associated antigens (TAA) coupled to or administered with a replication competent oncolytic adenovirus. In certain aspects the antigens are presented as fusion proteins with adenovirus coat proteins. In other aspects the antigens are covalently or non-covalently bound to the coat of an adenovirus. Covalently bound antigens can be chemically attached to the adenovirus coat by chemical linkers. Non-covalently attached antigens can be bound to the coat by affinity between the antigen or a binding moiety attached to the antigen and the adenovirus coat proteins or binding moieties attached to the coat proteins. In other aspects, the adenovirus can be formulated with a plurality antigens that are co-administered with an adenovirus composition.

Certain embodiments are directed to methods of treating cancer comprising administering to a tumor a replication competent adenovirus and one or more tumor associated antigens. In certain aspects, the replication competent adenovirus is a delta-24 adenovirus. In other aspects the coat proteins of the delta-24 adenovirus are coupled to one or more tumor associated antigens. In certain aspects the tumor associated antigens are presented as fusion proteins or protein chimeras on the surface of the adenovirus. As used herein, "chimera" or "chimeric" refers to a single transcription unit possessing multiple components, often but not necessarily from different proteins. As used herein, "chimeric" is used to refer to coding sequence that codes for adenovirus proteins that have been genetically engineered to result in a protein comprising all or part of an adenovirus coat protein having a heterologous segment comprising a tumor associated antigen. In another aspect, the antigens are covalently attached via chemical linkers to the coat of an adenovirus. In still other aspects, the antigens are formulated with a replication competent adenovirus and co-administered with the virus. In other aspects, the antigens may be administered before or after treatment with the adenovirus. In certain aspects the antigens are administered with an immune stimulant or enhancer.

In certain embodiments, an adenovirus is provided that expresses a plurality of tumor antigens on its surface. In certain aspects, 2, 3, 4, or 5 antigens are expressed on the surface of the adenovirus, for example, by inserting nucleic acid encoding each antigen into a separate gene encoding an adenovirus surface protein. The tumor antigens can be expressed as part of the capsid or fiber, or produced as exogenous proteins linked to autophagy-related proteins such as LC3 to increase the presentation of the exogenous protein during the adenoviral infection and replication. Targeting multiple antigens will help generate a consistent and effective immune response.

Tumor associated antigens (TAA) include, but are not limited to alphafetoprotein (AFP), melanoma associated antigen—MAGE-1, MAGE-2, MAGE-3, carcinoembryonic antigen (CEA) (IIGYVIGTQQATPGPAYSGREII, SEQ ID NO:1), Tyrosinase (Tyr), midkin (MK), BAGE, CASP-8, β-catenin, CA-125, CDK-1, ESO-1, gp75, gp100, MART-1, mucins (MUC-1), MUM-1, p53, PAP, PSA, PSMA, ras, trp-1, HER-2, TRP-2, IL13R alpha, AIM-3, or NY-ESO1. In certain aspects, the TAA are C9orf112, SART1, BRAP, RTN4, GLEA2, TNKS2, KIAA0376, ING4, HSPH1, C13orf24, RBPSUH, C6orf153, NKTR, NSEP1, U2AF1L, CYNL2, TPR, SOX2, or GOLGA. The adenovirus may express the full length tumor associated antigen or an immunogenic peptide thereof.

Other tumor associated antigens include, without limitation, tumor associated antigens that have been identified as occurring in patients with brain cancers such as gliomas representative examples of which include: AIM2 (absent in melanoma 2), BMI1 (BMI1 polycomb ring finger oncogene), COX-2 (cyclooxygenase-2), TRP-1 (tyrosine related protein 2) TRP-2 (tyrosine related protein 2), GP 100 (glycoprotein 100), EGFRvIII (epidermal growth factor receptor variant III), EZH2 (enhancer of zeste homolog 2), LICAM (human L1 cell adhesion molecule), Livin, Livinβ, MRP-3 (multidrug resistance protein 3), Nestin, OLIG2 (oligodendrocyte transcription factor), SOX2 (SRY-related HMG-box 2), ART1 (antigen recognized by T cells 1), ART4 (antigen recognized by T cells 4), SART1 (squamous cell carcinoma antigen recognized by T cells 1), SART2, SART3, B-cyclin, b-catenin, Gli1 (glioma-associated oncogene homlog 1), Cav-1 (caveolin-1), cathepsin B, CD74 (cluster of Differentiation 74), E-cadherin (epithelial calcium-dependent adhesion), EphA2/Eck (EPH receptor A2/epithelial kinase), Fra-1/Fosl 1 (fos-related antigen 1), GAGE-1 (G antigen 1), Ganglioside/GD2, GnT-V, β1,6-N (acetylglucosaminyltransferase-V), Her2/neu (human epidermal growth factor receptor 2), Ki67 (nuclear proliferation-associated antigen of antibody Ki67), Ku70/80 (human Ku heterodimer proteins subunits), IL-13Ra2 (interleukin-13 receptor subunit alpha-2), MAGE-A (melanoma-associated antigen 1), MAGE-A3 (melanoma-associated antigen 3), NY-ESO-1 (New York oesophageal squamous cell carcinoma 1), MART-1 (melanoma antigen recognized by T cells), PROX1 (prospero homeobox protein 1), PSCA (prostate stem cell antigen), SOX10 (SRY-related HMG-box 10), SOX11, Survivin, UPAR (urokinase-type plasminogen activator receptor, and WT-1 (Wilms' tumor protein 1). The adenovirus may express the full length tumor associated antigen or an immunogenic peptide thereof.

In certain aspects, the adenovirus can express a tumor-associated antigen from a heterologous nucleic acid incorporated into the adenoviral genome. The heterologous nucleic acid can be under the control of an adenoviral or heterologous promoter. A "heterologous" region of the construct is an identifiable segment of nucleic acid within a larger nucleic acid molecule that is not found in association with the larger molecule in nature.

Epidermal growth factor receptor (EGFR) is a 170 kDa glycoprotein encoded by the c-erb B proto-oncogene (Ullrich et al., Nature 309:418-425 (1984). This oncogene is activated in a variety of cancers, and is amplified in about 40% of malignant gliomas. An EGF receptor mutant (known as the type III mutant or EGFRvIII), comprising a 267 amino acid in-frame deletion in the extracellular domain that creates a novel junction, is commonly found in human cancers but is not expressed in any normal tissues. The novel junction created by the deletion in EGFRvIII is immunogenic. The sequence of EGFRvIII is described in U.S. Pat. No. 6,455,498, the content of which is hereby incorporated by reference. Immunogenic EGFRvIII include those described in U.S. Patent Application Publication No. 2009/0155282, the content of which is hereby incorporated by reference, particularly those at paragraph [0362] and Tables 4.1-4.3.

In a preferred embodiment, an adenovirus is provided comprising a surface protein containing an immunogenic EGFRvIII epitope. In one aspect, nucleic acid encoding full length EGFRvIII or an immunogenic peptide thereof is inserted into a gene encoding an adenovirus surface protein (e.g. the native gene may be modified by PCR mutagenesis to include the epitope) whereby the adenovirus expresses a chimeric surface protein comprising the EGFRvIII epitope. Thus, the invention provides a recombinant adenovirus having a genome comprising a (heterologous) nucleic acid encoding EGFRvIII or an immunogenic peptide thereof and its use in treating cancer. In one aspect, EGFRvIII or an immunogenic peptide thereof is inserted into the gene encoding the fiber protein, preferably in the H1 loop. This region of adenovirus has been demonstrated to be useful for antigen expression (Krause A. et al., J. Virol., 80:5523-30 (2006)). Nucleic acid encoding EGFRvIII or an immunogenic peptide thereof may be inserted into genes encoding one or more surface proteins of any adenovirus. In one aspect, the adenovirus is Delta-24. The term "immunogenic EGFRvIII peptide" as used herein means a peptide of suitable length e.g. at least 10 or 12 amino acids and up to 15, 20, 25 or 30 amino acids or more which spans the mutated splice junction of the corresponding EGFRvIII protein, preferably human EGFRvIII. In a preferred embodiment, the nucleic acid inserted into an adenovirus surface protein encodes an 8-20 amino acid peptide consisting of, consisting essentially of, or comprising the sequence EKKGNYVV (SEQ ID NO: 2). For example, the peptide may have a sequence selected from the group consisting of LEEKKGNY (SEQ ID NO: 3), LEEKKGNYVVT (SEQ ID NO: 4), LEEKKGNYVVTDH (SEQ ID NO: 5), or LEEKKGNYVVTDHC (SEQ ID NO: 6). In a particularly preferred embodiment, the EGFRvIII immunogenic peptide is LEEKKGNYVVT (SEQ ID NO: 4) and is inserted into the into the gene encoding the fiber protein, preferably in the H1 loop. In other embodiments, nucleic acid encoding the entire EGFRvIII extracellular domain is inserted into a gene encoding a surface protein of the adenovirus.

In other preferred embodiments, the invention provides a recombinant adenovirus having a genome comprising a (heterologous) nucleic acid encoding MAGE or an immunogenic peptide thereof and its use in treating cancer. Preferably, the nucleic acid encoding MAGE or an immunogenic peptide thereof is inserted into a gene encoding a surface protein, whereby the adenovirus expresses a chimeric surface protein comprising MAGE or an immunogenic peptide thereof. In one aspect, nucleic acid encoding MAGE or an immunogenic peptide thereof is inserted into a deleted E3 region of the adenovirus. Nucleic acid encoding MAGE or an immunogenic peptide thereof may be inserted into genes encoding one or more surface proteins of any adenovirus. In one aspect, the adenovirus is Delta-24. In other aspects the cancer is a primary or metastatic brain tumor.

In other preferred embodiments, the invention provides a recombinant adenovirus having a genome comprising a (heterologous) nucleic acid encoding NY-ESO-1 (GenBank U87459.1) or an immunogenic peptide thereof (e.g. SLLMWITQCFLPVF (SEQ ID NO: 7)) and its use in treating cancer. Preferably, the nucleic acid encoding NY-ESO-1 or an immunogenic peptide thereof is inserted into a gene encoding a surface protein, whereby the adenovirus expresses a chimeric surface protein comprising the NY-ESO-1 or an immunogenic peptide thereof. In one aspect, nucleic acid encoding NY-ESO-1 or an immunogenic peptide thereof is inserted into the hyper-variable region 5 of the gene encoding the hexon of the adenovirus. This region of adenovirus has been shown to be useful for antigen expression (Crawford-Miksza and Schnurr, J. Virol., 70:1836-44 (1996)). Nucleic acid encoding NY-ESO-1 or an immunogenic peptide thereof may be inserted into genes encoding one or more surface proteins of any adenovirus. In one aspect, the adenovirus is Delta-24. In other aspects, the cancer is a primary or metastatic brain tumor.

In a particularly preferred embodiment, the invention provides a recombinant adenovirus having a genome comprising: (a) nucleic acid encoding an immunogenic EGFRvIII peptide (e.g. LEEKKGNYVVT (SEQ ID NO: 4)) inserted into the gene encoding the H1 loop of the adenovirus fiber protein (b) nucleic acid encoding MAGE or an immunogenic peptide thereof inserted into a deleted E3 region of the adenovirus and (c) nucleic acid encoding NY-ESO-1 or an immunogenic peptide thereof inserted into the hyper-variable region 5 of the gene encoding the adenovirus hexon protein, and its use in treating cancer. In one aspect, the adenovirus is Delta-24. In other aspects, the cancer is a primary or metastatic brian tumor.

Insertion of nucleic acids encoding the tumor antigens into adenovirus genes should be done "in frame" such that the virus expresses the tumor antigen on its surface.

Certain aspects do not require the complete resection of the tumor, which is a limiting factor in recruitment of patients in other approaches. Furthermore, certain aspects of the current methods and compositions have the potential to generate memory in the immune system and preventing or reducing the probability of tumor recurrence.

The term "replication competent adenoviral vector" refers to any adenoviral vector that is not deficient in any gene function required for viral replication in specific cells or tissues. The vector must is capable of replicating and being packaged, but might replicate only conditionally in specific cells or tissues.

The term "therapeutic benefit" or "treatment" refers to anything that promotes or enhances the well-being of the subject with respect to the medical treatment of his/her condition, which includes treatment of pre-cancer, cancer, and hyperproliferative diseases. A list of nonexhaustive examples of this includes extension of the subject's life by any period of time, decrease or delay in the neoplastic development of the disease, decrease in hyperproliferation, reduction in tumor growth, delay of metastases, reduction in cancer cell or tumor cell proliferation rate, and a decrease in pain to the subject that can be attributed to the subject's condition.

The term "glioma" refers to a tumor originating in the neuroglia of the brain or spinal cord. Gliomas are derived form the glial cell types such as astrocytes and oligodendrocytes, thus gliomas include astrocytomas and oligodendrogliomas, as well as anaplastic gliomas, glioblastomas, and ependymomas. Astrocytomas and ependymomas can occur in all areas of the brain and spinal cord in both children and adults. Oligodendrogliomas typically occur in the cerebral hemispheres of adults. Gliomas account for 75% of brain tumors in pediatrics and 45% of brain tumors in adults. Other brain tumors are meningiomas, ependymomas, pineal region tumors, choroid plexus tumors, neuroepithelial tumors, embryonal tumors, peripheral neuroblastic tumors, tumors of cranial nerves, tumors of the hemopoietic system, germ cell tumors, and tumors of the stellar region.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION

Figure 1:
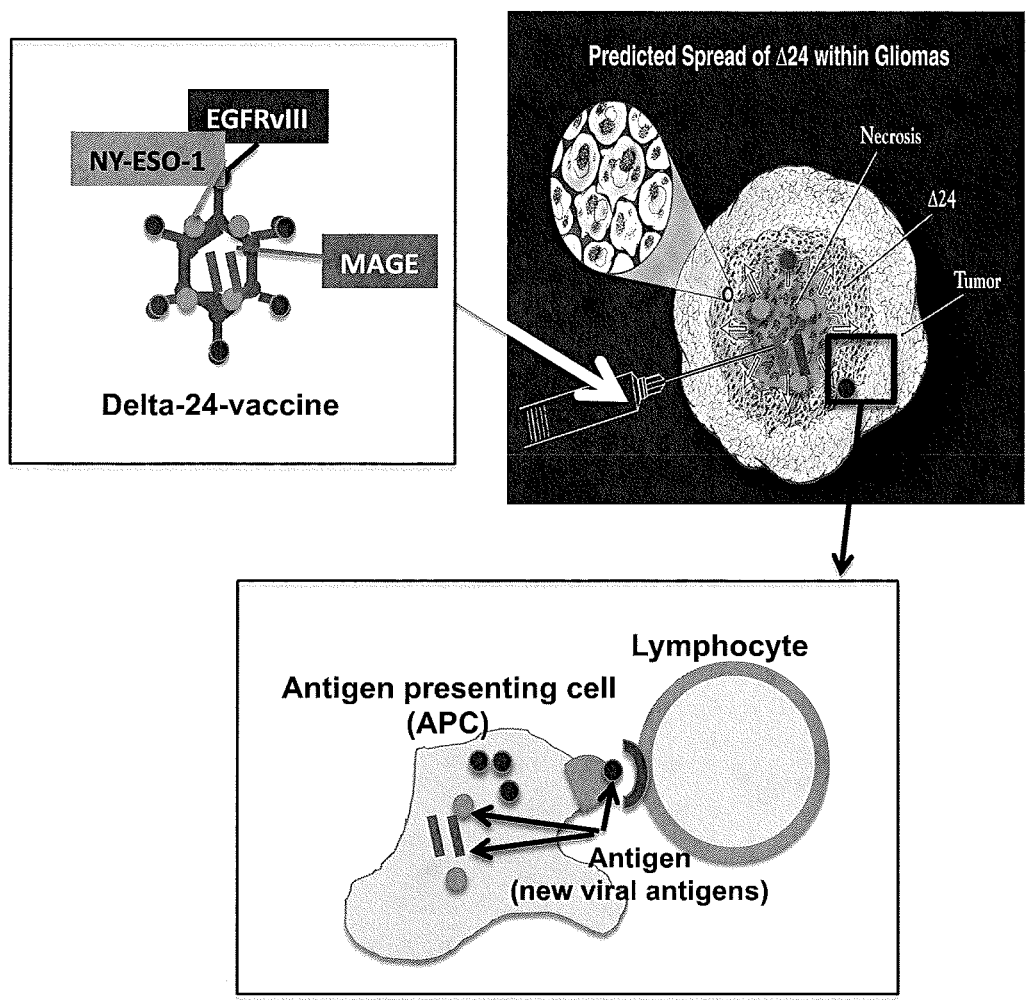
FIG. 1. The structure of adenovirus allows for modification of several regions of its genome to insert epitopes that will be presented as antigens or full length cDNAs to express proteins. The upper left panel depicts an adenovirus (Delta-24-vaccine) having a genome comprising nucleic acid encoding three separate tumor antigens (immunogenic EGFRvIII peptide, immunogenic NY-ESO-1 peptide and full length MAGE protein) inserted into three separate surface proteins (H1 loop of the fiber protein, hyper-variable region 5 of the hexon and deleted E3 region, respectively). These antigens will be expressed on the surface of the recombinant adenovirus without any decrease in oncolytic potency and without interference between expression of viral proteins. When administered to a patient with cancer, the adenovirus will induce tumor necrosis. Expression of these antigens in the inflammatory tumor microenvironment should recruit macrophages and other antigen presenting cells to trigger a "re-directed" anti-tumor immune response.
Figure 2:
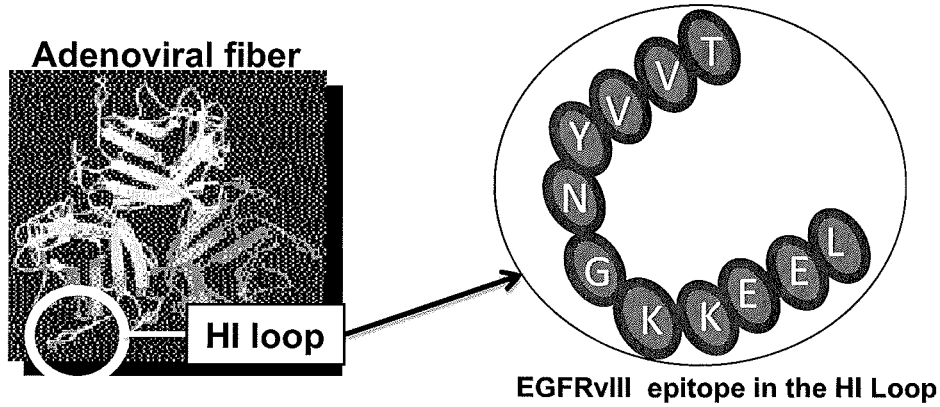
FIG. 2. Construction of a novel adenovirus expressing an immunogenic tumor antigen. Panel A. An immunogenic EGFRvIII peptide (LEEKKGNYVVT (SEQ ID NO: 4)) has been cloned in the H1 loop of Delta-24-vaccine fiber protein. Panel B. The technical strategy used to clone the peptide in the H1 loop has been described (Suzuki et al., Clin. Cancer Res. 7:120-6 (2001). The plasmid containing the fiber protein gene was modified using PCR mutagenesis to include (i.e. insert) the peptide and then subjected to homologous recombination in bacteria with the plasmid containing the rest of the sequence of the adenovirus including the Delta-24 mutation. The final product was then amplified using 293 cells.
Figure 2:
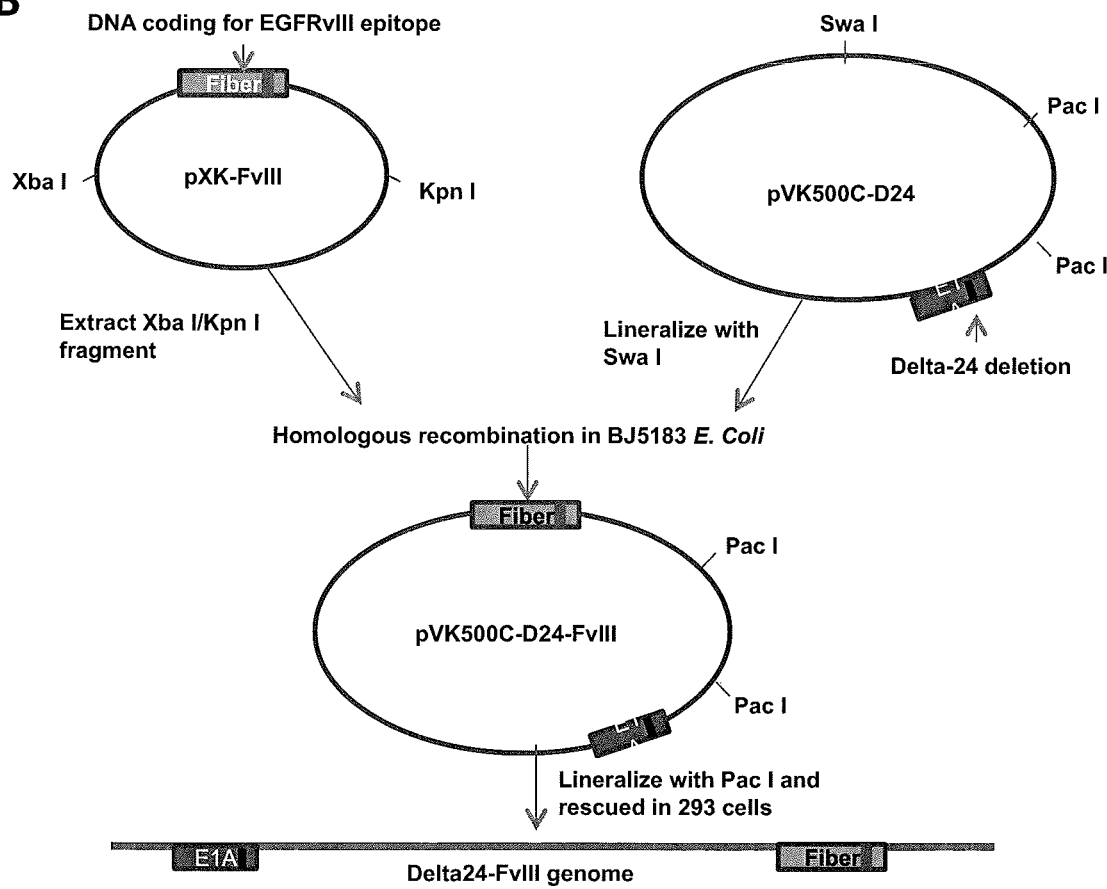
Figure 3:
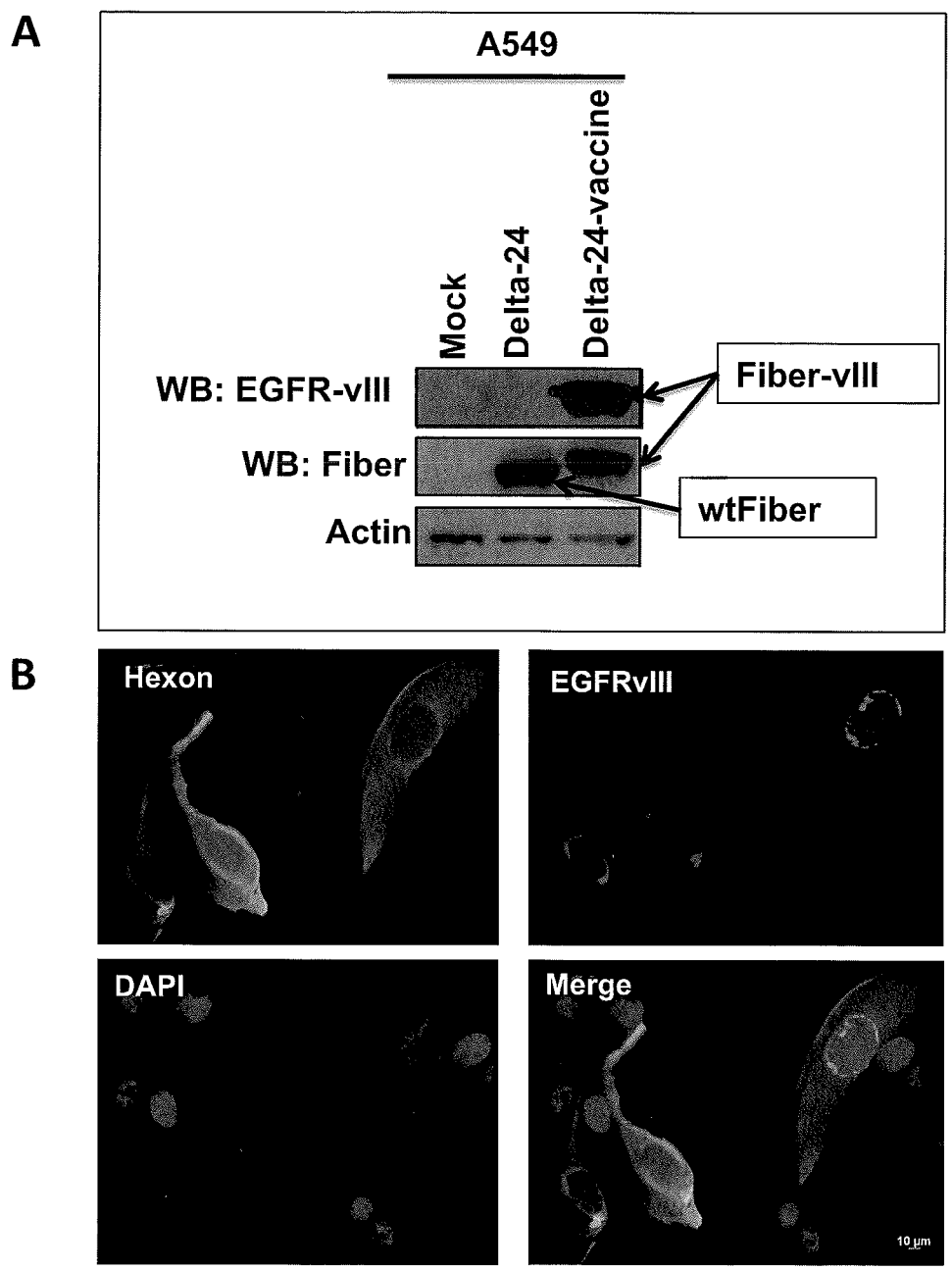
FIG. 3. Expression of the immunogenic EGFRvIII peptide. Panel A illustrates a Western blot demonstrating that the EGFRvIII epitope is expressed on the surface of the modified Delta-24 adenovirus. Delta-24 adenovirus expressing fiber protein containing the EGFRvIII epitope (D24-EG-FRvIII), constructed according to FIG. 2, were subjected to cell lysate, protein extraction and Western blot analyses. Using antibodies against the adenovirus fiber protein or the EGFRvIII peptide, high expression of the EGFRvIII antigen confirmed. Actin was used as a loading control. Panel B illustrates immunofluorescence analyses of cancer cells infected with D24-EGFRvIII using antibody against the virus (Hexon), antibody against EGFRvIII peptide (EG-FRvIII) and 4',6-diamidino-2-phenylindole (DAPI). The images illustrate that cells infected with D24-EGFRvIII express the EGFRvIII peptide. DNA staining (DAPI) confirms that only the infected cells express the EGFRvIII peptide. The adenovirus capsids are assembled in the nucleus.
Figure 4:
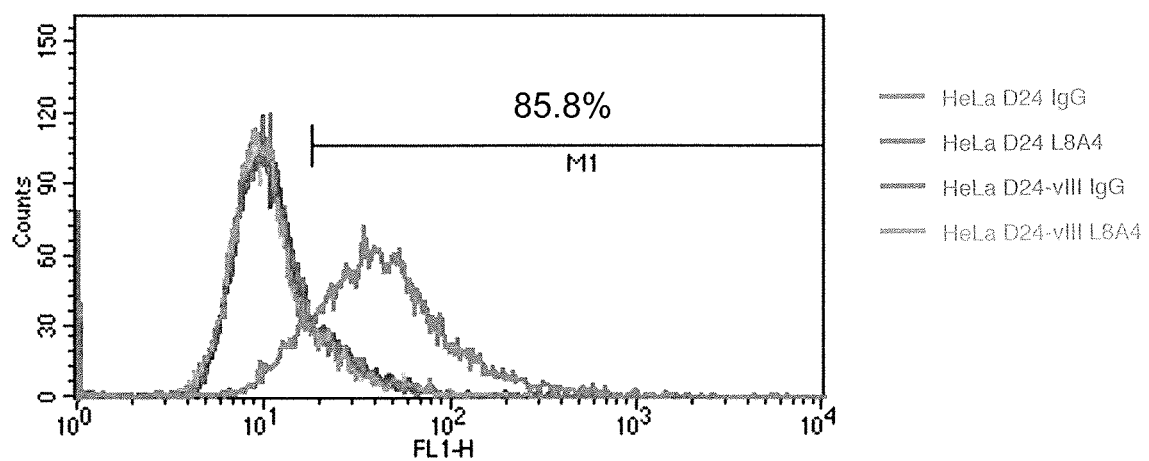
FIG. 4. Assessment of the presentation of EGFRvIII epitope on the surface of D24-EGFRvIII-infected cells. HeLa cells were infected with the indicated adenovirus at an m.o.i. of 50 pfu/cell. 48 hours later the cells were stained with mouse monoclonal anti-EGFRvIIII antibody L8A4. The percentage of cells with EGFRvIII epitope on the surface was assessed with flow cytometry. D24 (Delta-24 adenovirus not expressing the EGFRvIII epitope) was used as a control for virus infection. Mouse IgG was used as a negative control for antibody.
Figure 5:
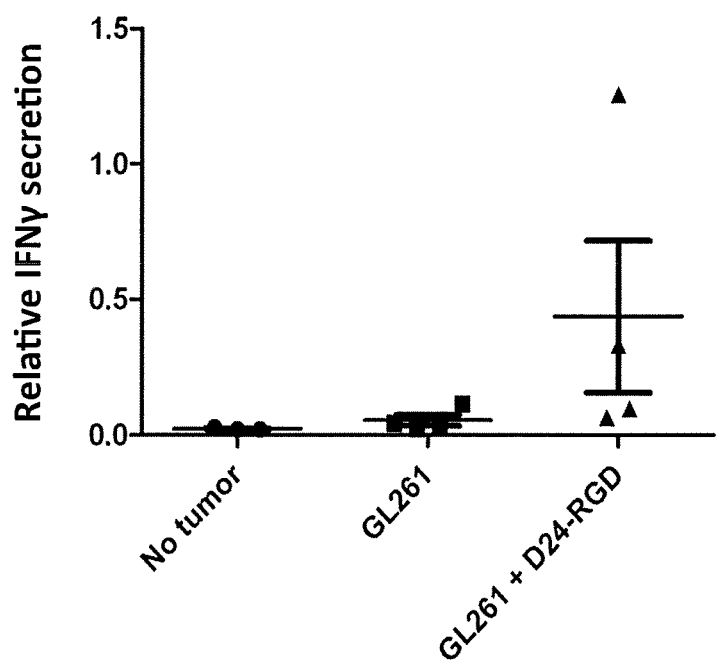
FIG. 5. Delta-24-RGD induces anti-tumor immune response. GL261 cells were implanted intracranially in C57BL/6 mice. Delta-24-RGD was injected into the tumor at days 7 and 9. 7 days after last viral injection, mouse splenocytes were isolated and co-cultured with GL261 cells. The IFN-γ secreted by lymphocytes was measured by ELISA.
Figure 6:
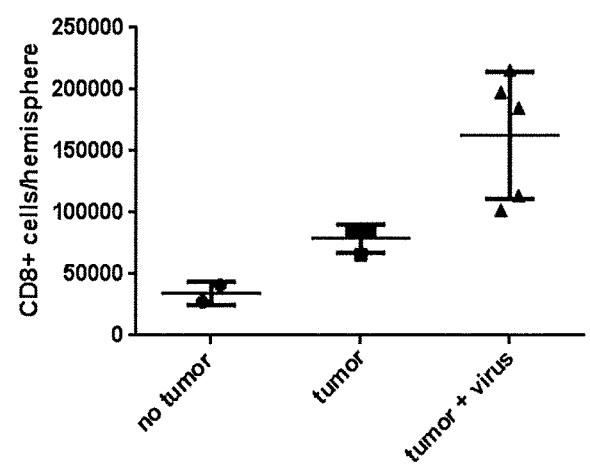
FIG. 6. Delta-24-RGD treatment resulted in recruitment of CD8+ and CD4+ T cells into tumor site. GL261 cells were implanted intracranially in C57BL/6 mice. Delta-24-RGD was injected into the tumor at days 7 and 10. 7 days after the last viral injection, lymphocytes were isolated from the brain and characterized by flow cytometry.
Figure 6:
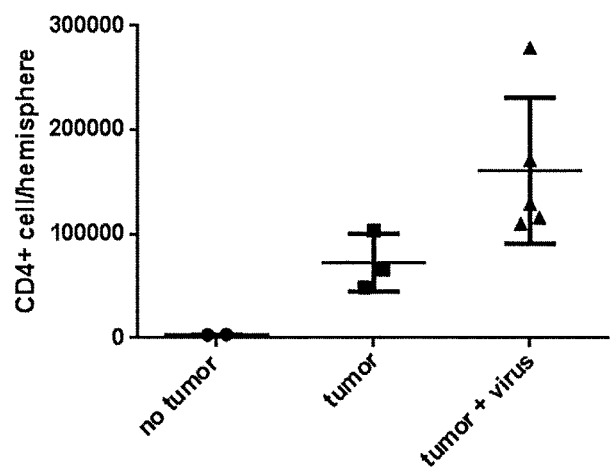

Methods and compositions of the present invention include the construction and verification of adenoviral vaccines that elicit an immune response against tumor associated antigens to enhance anti-tumor therapy.

I. Adenoviral Vaccines

Adenovirus (Ad) is a large (~36 kb) DNA virus that infects humans, but which display a broad host range. Physically, adenovirus is an icosahedral virus containing a double-stranded, linear DNA genome. There are approximately 50 serotypes of human adenovirus, which are divided into six families based on molecular, immunological, and functional criteria. By adulthood, virtually every human has been infected with the more common adenovirus serotypes, the major effect being cold-like symptoms.

Adenoviral infection of host cells results in adenoviral DNA being maintained episomally, which reduces the potential genotoxicity associated with integrating vectors. Also, adenoviruses are structurally stable, and no genome rearrangement has been detected after extensive amplification. Adenovirus can infect virtually most epithelial cells regardless of their cell cycle stage. So far, adenoviral infection appears to be linked only to mild disease such as acute respiratory disease in humans Members of any of the 57 human adenovirus serotypes (HAdV-1 to 57) may incorporate, be coupled-to or be administered with one or more tumor associated antigen peptides according to the invention. Human Ad5 is well characterized genetically and biochemically (GenBank M73260; AC_000008). Thus, in a preferred embodiment, the adenovirus is a replication competent Ad5 serotype or a hybrid serotype comprising an Ad5 component. The adenovirus may be a wild type strain or may be genetically modified to enhance tumor selectivity, for example by attenuating the ability of the virus to replicate within normal quiescent cells without affecting the ability of the virus to replicate in tumor cells. Non-limiting examples of adenoviruses encompassed by the present invention include Delta-24, Delta-24-RGD, ICOVIR-5, ICOVIR-7, ONYX-015, ColoAd1, H101 and AD5/3-D24-GMCSF. Onyx-015 is a hybrid of virus serotype Ad2 and Ad5 with deletions in the E1B-55K and E3B regions to enhance cancer selectivity. H101 is a modified version of Onyx-015. ICOVIR-5 and ICOVIR-7 comprise an Rb-binding site deletion of E1A and a replacement of the E1A promoter by an E2F promoter. ColoAd1 is a chimeric Add11p/Ad3 serotype. AD5/3-D24-GMCSF (CGTG-102) is a serotype 5/3 capsid-modified adenovirus encoding GM-CSF (the Ad5 capsid protein knob is replaced with a knob domain from serotype 3).

In one particularly preferred embodiment, the adenovirus is Delta-24 or Delta-24-RGD. Delta-24 is described in U.S. Patent Application Publication Nos. 20030138405, and 20060147420, each of which are incorporated herein by reference. The Delta-24 adenovirus derived from adenovirus type 5 (Ad-5) and contains a 24-base-pair deletion within the CR2 portion of the E1A gene that encompasses the area responsible for binding Rb protein (nucleotides 923-946) corresponding to amino acids 120-127 in the encoded E1A protein (Fueyo J et al., Oncogene, 19:2-12 (2000)). Delta-24-RGD further comprises an insertion of the RGD-4C sequence (which binds strongly to αvβ3 and αvβ5 integrins) into the H1 loop of the fiber knob protein (Pasqualini R. et al., Nat Biotechnol, 15:542-546 (1997)). The E1A deletion increases the selectivity of the virus for cancer cells; the RGD-4C sequence increases the infectivity of the virus in gliomas.

Significant antitumor effects of Delta-24 have been shown in cell culture systems and in malignant glioma xenograft models. Delta-24-RGD has shown surprising anti-tumor effects in a Phase 1 clinical trial and is currently the subject of additional clinical trials. Aspects of the current invention are directed at enhancing this anti-tumor efficacy.

The infectious cycle of the adenovirus takes place in 2 steps: the early phase which precedes initiation of the replication of the adenoviral genome, and which permits production of the regulatory proteins and proteins involved in the replication and transcription of the viral DNA, and the late phase which leads to the synthesis of the structural proteins. The early genes are distributed in 4 regions that are dispersed in the adenoviral genome, designated E1 to E4 (E denotes "early"). The early regions comprise at least-six transcription units, each of which possess their own promoters. The expression of the early genes is itself regulated, some genes being expressed before others. Three regions, E1, E2, and E4 are essential to replication of the virus. Thus, if an adenovirus is defective for one of these functions this protein will have to be supplied in trans, or the virus cannot replicate.

The E1 early region is located at the 5'end of the adenoviral genome, and contains 2 viral transcription units, E1A and E1B. This region encodes proteins that participate very early in the viral cycle and are essential to the expression of almost all the other genes of the adenovirus. In particular, the E1A transcription unit codes for a protein that transactivates the transcription of the other viral genes, inducing transcription from the promoters of the E1B, E2A, E2B, E3, E4 regions and the late genes. Typically, exogenous sequences are integrated in place of all or part of the E3 region The adenovirus enters the permissive host cell via a cell surface receptor, and it is then internalized. The viral DNA associated with certain viral proteins needed for the first steps of the replication cycle enters the nucleus of the infected cells, where transcription is initiated. Replication of the adenoviral DNA takes place in the nucleus of the infected cells and does not require cell replication. New viral particles or virions are assembled after which they are released from the infected cells, and can infect other permissive cells.

Aspects of the invention include the development, the production, and the evaluation of a vaccine comprising one or more tumor associated antigen (TAA). The adenoviral vector system not only provides a viable delivery vehicle, but also may elicit an anti-tumor immune response. The adenovirus is well-established for use in gene transfer in several therapeutic applications including anti-cancer immunotherapy and cardiovascular revascularization.

The adenovirus is an attractive delivery system. Embodiments of the invention can utilize a suspension cell process with average yields of $1\times10^{16}$ viral particles per batch. The process can be free of or essentially free of protein, serum, and animal derived components making it suitable for a broad range of both prophylactic and therapeutic vaccine products.

Several factors favor the use of oncolytic adenoviruses for the treatment of brain tumors. First, gliomas are typically localized, and therefore an efficient local approach should be enough to cure the disease. Second, gliomas harbor several populations of cells expressing different genetic abnormalities. Thus, the spectrum of tumors sensitive to the transfer of a single gene to cancer cells may be limited. Third, replication competent adenoviruses can infect and destroy cancer cells that are arrested in $G_0$. Since gliomas invariably include non-cycling cells, this property is important. Finally, the p16-Rb pathway abnormal in the majority of gliomas, thus making the Delta-24 strategy appropriate for most of these tumors. Although the loss of the retinoblastoma tumor suppressor gene function has been associated with the causes of various types of tumors and is not limited to treatment of gliomas.

If an adenovirus has been mutated so that it is unable to replicate or is conditionally replicative (replication-competent under certain conditions), a helper cell may be required for viral replication. When required, helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, for example Vero cells or other monkey embryonic mesenchymal or epithelial cells. In certain aspects a helper cell line is 293. Various methods of culturing host and helper cells may be found in the art, for example Racher et al., 1995.

In certain aspects, the adenovirus is typically replication-competent in cells with a mutant Rb pathway. After transfection, adenoviral plaques are isolated from the agarose-overlaid cells and the viral particles are expanded for analysis. For detailed protocols the skilled artisan is referred to Graham and Prevac, 1991.

Alternative technologies for the generation of adenovirus vectors include utilization of the bacterial artificial chromosome (BAC) system, in vivo bacterial recombination in a recA+bacterial strain utilizing two plasmids containing complementary adenoviral sequences, and the yeast artificial chromosome (YAC) system (PCT publications 95/27071 and 96/33280, which are incorporated herein by reference).

Adenovirus is easy to grow and manipulate and exhibits broad host range in vitro and in vivo. This group of viruses can be obtained in high titers (e.g., greater than $10^9$ plaque forming units (pfu) per ml), and they are highly infective. The life cycle of adenovirus does not require integration into the host cell genome.

Modifications of oncolytic adenovirus described herein may be made to improve the ability of the oncolytic adenovirus to treat cancer. Such modifications of an oncolytic adenovirus have been described by Jiang et al. (Curr Gene Ther. 2009 Oct. 9(5):422-427), see also U.S. Patent Application No. 20060147420, each of which are incorporated herein by reference.

The absence or the presence of low levels of the coxsackievirus and adenovirus receptor (CAR) on several tumor types can limit the efficacy of the oncolytic adenovirus. Various peptide motifs may be added to the fiber knob, for instance an RGD motif (RGD sequences mimic the normal ligands of cell surface integrins), Tat motif, polylysine motif, NGR motif, CTT motif, CNGRL motif, CPRECES motif or a strept-tag motif (Rouslahti and Rajotte, 2000). A motif can be inserted into the HI loop of the adenovirus fiber protein. Modifying the capsid allows CAR independent target cell infection. This allows higher replication, more efficient infection, and increased lysis of tumor cells (Suzuki et al., 2001, incorporated herein by reference). Peptide sequences that bind specific human glioma receptors such as EGFR or uPR may also be added. Specific receptors found exclusively or preferentially on the surface of cancer cells may be used as a target for adenoviral binding and infection, such as EGFRvIII.

II. Expression Cassettes

In certain embodiments of the present invention, the methods set forth herein involve nucleic acid sequences encoding a TAA wherein the nucleic acid is comprised in an "expression cassette." The term "expression cassette" is meant to include any type of genetic construct containing a nucleic acid coding for a gene product (e.g., an antigenic determinant) in which part or all of the nucleic acid encoding sequence is capable of being transcribed.

Promoters and Enhancers—In order for the expression cassette to effect expression of a transcript, the nucleic acid encoding gene will be under the transcriptional control of a promoter. A "promoter" is a control sequence that is a region of a nucleic acid sequence at which initiation and rate of transcription are controlled. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

Any promoter known to those of ordinary skill in the art that would be active in a cell in a subject is contemplated as a promoter that can be applied in the methods and compositions of the present invention. One of ordinary skill in the art would be familiar with the numerous types of promoters that can be applied in the present methods and compositions. In certain embodiments, for example, the promoter is a constitutive promoter, an inducible promoter, or a repressible promoter. The promoter can also be a tissue selective promoter. A tissue selective promoter is defined herein to refer to any promoter that is relatively more active in certain tissue types compared to other tissue types. Examples of promoters include the CMV promoter.

The promoter will be one that is active in a cell and expression from the promoter results in the presentation of an antigenic determinant to a subject's immune system. For instance, where the cell is an epithelial cell the promoter used in the embodiment will be one having activity in that particular cell type.

A promoter may be one naturally associated with a gene or sequence, as may be obtained by isolating the 5'-non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™ (see U.S. Pat. Nos. 4,683,202 and 5,928,906, each incorporated herein by reference).

Naturally, it will be important to employ a promoter and/or enhancer that effectively directs the expression of the DNA segment in the cell type, organelle, and organism chosen for expression. Those of skill in the art of molecular biology generally understand the use of promoters, enhancers, and cell type combinations for protein expression, for example, see Sambrook et al. (2001), incorporated herein by reference. The promoter may be heterologous or endogenous.

The particular promoter that is employed to control the expression of the nucleic acid of interest is not believed to be critical, so long as it is capable of expressing the polynucleotide in the targeted cell at sufficient levels. Thus, where a human cell is targeted, it is preferable to position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used. The use of other viral or mammalian cellular or bacterial phage promoters, which are well-known in the art to achieve expression of polynucleotides, is contemplated as well, provided that the levels of expression are sufficient to produce an immune response.

Additional examples of promoters/elements that may be employed, in the context of the present invention include the following, which is not intended to be exhaustive of all the possible promoter and enhancer elements, but, merely, to be exemplary thereof.

Immunoglobulin Heavy Chain (Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990); Immunoglobulin Light Chain (Queen et al., 1983; Picard et al., 1984); T Cell Receptor (Luria et al., 1987; Winoto et al., 1989; Redondo et al.; 1990); HLA DQ a and/or DQ β(Sullivan et al., 1987); β Interferon (Goodbourn et al., 1986; Fujita et al., 1987; Goodbourn et al., 1988); Interleukin-2 (Greene et al., 1989); Interleukin-2 Receptor (Greene et al., 1989; Lin et al., 1990); MHC Class II (Koch et al., 1989); MHC Class II HLA-DRa (Sherman et al., 1989); β-Actin (Kawamoto et al., 1988; Ng et al.; 1989); Muscle Creatine Kinase (MCK) (Jaynes et al., 1988; Horlick et al., 1989; Johnson et al., 1989); Prealbumin (Transthyretin) (Costa et al., 1988); Elastase I (Omitz et al., 1987); Metallothionein (MTII) (Karin et al., 1987; Culotta et al., 1989); Collagenase (Pinkert et al., 1987; Angel et al., 1987); Albumin (Pinkert et al., 1987; Tronche et al., 1989, 1990); α-Fetoprotein (Godbout et al., 1988; Campere et al., 1989); t-Globin (Bodine et al., 1987; Perez-Stable et al., 1990); β-Globin (Trudel et al., 1987); c-fos (Cohen et al., 1987); c-HA-ras (Triesman, 1986; Deschamps et al., 1985); Insulin (Edlund et al., 1985); Neural Cell Adhesion Molecule (NCAM) (Hirsh et al., 1990); α1-Antitrypsin (Latimer et al., 1990); H2B (TH2B) Histone (Hwang et al., 1990); Mouse and/or Type I Collagen (Ripe et al., 1989); Glucose-Regulated Proteins (GRP94 and GRP78) (Chang et al., 1989); Rat Growth Hormone (Larsen et al., 1986); Human Serum Amyloid A (SAA) (Edbrooke et al., 1989); Troponin I (TN I) (Yutzey et al., 1989); Platelet-Derived Growth Factor (PDGF) (Pech et al., 1989); Duchenne Muscular Dystrophy (Klamut et al., 1990); SV40 (Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988); Polyoma (Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988); Retroviruses (Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989); Papilloma Virus (Campo et al., 1983; Lusky et al., 1983; Wilkie, 1983; Spalholz et al., 1985; Lusky et al., 1986; Cripe et al., 1987; Gloss et al., 1987; Hirochika et al., 1987; Stephens et al., 1987); Hepatitis B Virus (Bulla et al., 1986; Jameel et al., 1986; Shaul et al., 1987; Spandau et al., 1988; Vannice et al., 1988); Human Immunodeficiency Virus (Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989); Cytomegalovirus (CMV) (Weber et al., 1984; Boshart et al., 1985; Foecking et al., 1986); Gibbon Ape Leukemia Virus (Holbrook et al., 1987; Quinn et al., 1989).

Enhancers were originally detected as genetic elements that increased transcription from a promoter located at a distant position on the same molecule of DNA. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have very similar modular organization. Additionally, any promoter/enhancer combination (as per the Eukaryotic Promoter Data Base EPDB) could also be used to drive expression of a gene. Further selection of a promoter that is regulated in response to specific physiologic signals can permit inducible expression of a construct. For example, with the polynucleotide under the control of the human PAI-1 promoter, expression is inducible by tumor necrosis factor. Examples of inducible elements, which are regions of a nucleic acid sequence that can be activated in response to a specific stimulus include (Element/Inducer): MT II/Phorbol Ester (TFA) or Heavy metals (Palmiter et al., 1982; Haslinger et al., 1985; Searle et al., 1985; Stuart et al., 1985; Imagawa et al., 1987, Karin et al., 1987; Angel et al., 1987b; McNeall et al., 1989); MMTV (mouse mammary tumor virus)/Glucocorticoids (Huang et al., 1981; Lee et al., 1981; Majors et al., 1983; Chandler et al., 1983; Ponta et al., 1985; Sakai et al., 1988); β-Interferon/poly(rI)x or poly(rc) (Tavernier et al., 1983); Adenovirus 5 E2/E1A (Imperiale et al., 1984); Collagenase/Phorbol Ester (TPA) (Angel et al., 1987a); Stromelysin/Phorbol Ester (TPA) (Angel et al., 1987b); SV40/Phorbol Ester (TPA) (Angel et al., 1987b); Murine MX Gene/Interferon, Newcastle Disease Virus (Hug et al., 1988); GRP78 Gene/A23187 (Resendez et al., 1988); α-2-Macroglobulin/IL-6 (Kunz et al., 1989); Vimentin/Serum (Rittling et al., 1989); MHC Class I Gene H-2κb/Interferon (Blanar et al., 1989); HSP70/E1A, SV40 Large T Antigen (Taylor et al., 1989, 1990a, 1990b); Proliferin/Phorbol Ester-TPA (Mordacq et al., 1989); Tumor Necrosis Factor/PMA (Hensel et al., 1989); and Thyroid Stimulating Hormone a Gene/Thyroid Hormone (Chatterjee et al., 1989).

Initiation Signals—A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

IRES—In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages (see U.S. Pat. Nos. 5,925,565 and 5,935,819).

Multiple Cloning Sites—Expression cassettes can include a multiple cloning site (MCS), which is a nucleic acid region that contains multiple restriction enzyme sites, any of which can be used in conjunction with standard recombinant technology to digest the vector.

Polyadenylation Signals—In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

Other Expression Cassette Components—In certain embodiments of the invention, cells infected by the adenoviral vector may be identified in vitro by including a reporter gene in the expression vector. Generally, a selectable reporter is one that confers a property that allows for selection. A positive selectable reporter is one in which the presence of the reporter gene allows for its selection, while a negative selectable reporter is one in which its presence prevents its selection. An example of a positive selectable marker is a drug resistance marker (genes that confer resistance to neomycin, puromycin, hygromycin, DHFR, GPT, zeocin and histidinol). Other types of reporters include screenable reporters such as GFP.

Embodiments of the invention can use current adenoviral platform technologies designed to create vaccines by preparing an adenoviral nucleic acid comprising a heterologous nucleic acid segment that encodes a tumor associated antigen. Aspects of the adenoviral vaccine construction include inserting genetic material into an adenoviral vector and confirming the construct through characterization and sequencing of the nucleic acid, virus and virus product. The adenoviral vaccine is then put through a series of feasibilities studies designed to assess scalability.

III. Cancer Antigens

The present invention is useful in the development of genetic anti-cancer immunization and lysis of a tumor. The development of anti-cancer vaccination strategies has been rationalized by the recent identification of tumor associated antigens (TAA) which may be recognized by the immune system as specific markers of cancer cells, thereby identifying these cells as the targets. These tumor associated antigens include proteins encoded by genes with mutations or rearrangements unique to tumor cells, reactivated embryonic genes, tissue-specific differentiation antigens, and a number of other self proteins. However, despite the identification of these targets, development of effective anti-cancer vaccination strategies has been limited to a large extent by the lack of means for successful vaccination against these weak, self-derived antigens. The generation of a potent anti-tumor associated antigen immune response is thus recognized as a key issue in the development of efficient anti-cancer immunization strategies.

The method of the present invention is effective in treating or preventing disease. Many diseases have specific antigens associated with the disease state. Such antigens or immunodominant epitopes of these antigens are used in immune recognition and ultimate elimination or control of the disease in a patient. Such antigens are referred to in the art as protective antigens.

The methods of the present invention may be used to treat cancers. Specific examples of cancer types include but are not limited to glioma, melanoma, metastases, adenocarcinoma, thyoma, lymphoma, sarcoma, lung cancer, liver cancer, colon cancer, non-Hodgkins lymphoma, Hodgkins lymphoma, leukemias, uterine cancer, breast cancer, prostate cancer, ovarian cancer, cervical cancer, bladder cancer, kidney cancer, pancreatic cancer and the like.

The term melanoma includes, but is not limited to, melanomas, metastatic melanomas, melanomas derived from either melanocytes or melanocytes related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome. Such melanomas in mammals may be caused by, chromosomal abnormalities, degenerative growth and developmental disorders, mitogenic agents, ultraviolet radiation (UV), viral infections, inappropriate tissue expression of a gene, alterations in expression of a gene, and presentation on a cell, or carcinogenic agents. The aforementioned cancers can be assessed or treated by methods of the present invention. In the case of cancer, a gene encoding an antigen associated with the cancer is incorporated into the recombinant virus genome or portion thereof along with a gene encoding one or more immunostimulatory molecules. The antigen associated with the cancer may be expressed on the surface of a cancer cell, may be secreted or may be an internal antigen. In one embodiment the antigen associated with the cancer is a tumor associated antigen (TAA) or portion thereof. Examples of TAA that may be used in the present invention include but are not limited to melanoma TAAs that include but are not limited to MART-1 (Kawakami et al. J. Exp. Med. 180:347-352, 1994), MAGE-1, MAGE-3, GP-100, (Kawakami et al. Proc. Nat'l. Acad. Sci. U.S.A. 91:6458-6462, 1994), CEA, TRP-1, TRP-2, P-15, and tyrosinase (Brichard et al. J. Exp. Med. 178:489, 1993) and the like.

In certain embodiments, an adenovirus will express a plurality of antigens on its surface. In certain aspects, 2, 3, 4, or 5 antigens can be expressed on the surface. The antigens can be expressed as part of the capsid or fiber, or produced as exogenous proteins linked to autophagy-related proteins such as LC3 to increase the presentation of the exogenous protein during the adenoviral infection and replication. Targeting multiple antigens will help generate a consistent and effective immune response. Tumor associated antigens (TAA) include, but are not limited to peptides of EGFRvIII, alphafetoprotein (AFP), melanoma associated antigen—MAGE-1, MAGE-2, MAGE-3, carcinoembryonic antigen (CEA) (IIGYVIGTQQATPGPAYSGREII, SEQ ID NO:1), Tyrosinase (Tyr), midkin (MK), BAGE, CASP-8, β-catenin, CA-125, CDK-1, ESO-1, gp75, gp100, MART-1, mucins (MUC-1), MUM-1, p53, PAP, PSA, PSMA, ras, trp-1, HER-2, TRP-2, IL13R alpha, AIM-3, NY-ESO1, C9orf112, SART1, BRAP, RTN4, GLEA2, TNKS2, KIAA0376, ING4, HSPH1, C13orf24, RBPSUH, C6orf153, NKTR, NSEP1, U2AF1L, CYNL2, TPR, SOX2, or GOLGA. The present invention is in no way limited to the genes encoding the above listed TAAs. Other TAAs are known to the skilled artisan and may be readily prepared by known methods, such as those disclosed in U.S. Pat. No. 4,514,506.

IV. Pharmaceutical Compositions

The present invention also provides a pharmaceutical composition comprising any composition of the present invention, and a pharmaceutically acceptable carrier. The present invention also provides a vaccine composition comprising any composition of the present invention. The vaccine composition may further comprise at least one adjuvant.

The present invention also provides a method of stimulating an anti-tumor immune response in a subject, comprising administering to a subject a composition of the present invention.

According to the present invention, an adenovirus in combination with an antigenic determinant is administered to a subject to induce an immune response for therapeutic or prophylatic purposes. Thus, in certain embodiments, the expression construct formulated in a composition that is suitable for this purpose. The phrases "pharmaceutically" or "pharmacologically acceptable" refer to compositions that do not produce adverse, allergic, or other untoward reactions when administered to an animal or a human. As used herein, "pharmaceutically acceptable carrier" includes any and all solvents, carriers, dispersion media, coatings, antibacterial and antifungal agents, isotonic and absorption delaying agents, and the like. The use of such media and agents for pharmaceutically active substances is well known in the art. Except insofar as any conventional media or agent is incompatible with the expression constructs of the present invention, its use in therapeutic compositions is contemplated. Supplementary active ingredients also can be incorporated into the compositions. For example, the supplementary active ingredient may be an additional immunogenic agent.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. If needed, various antibacterial an antifungal agents can be used, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically or prophylactically effective. For parenteral administration in an aqueous solution, the solution should be suitably buffered if necessary and the liquid diluent first rendered isotonic with sufficient saline or glucose. These particular aqueous solutions are especially suitable for intravascular and intratumoral administration. In this connection, sterile aqueous media, which can be employed will be known to those of skill in the art in light of the present disclosure.

Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by the FDA.

Dosage—An effective amount of the therapeutic or preventive agent is determined based on the intended goal, for example stimulation of an immune response against a tumor. Those of skill in the art are well aware of how to apply gene delivery in vivo and ex vivo situations. For viral vectors, one generally will prepare a viral vector stock. Depending on the kind of virus and the titer attainable, one will deliver at least about, at most about, or about $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles, or any value or range there between, to a subject. In other aspects, adenoviruses according to the invention may be administered in a single administration or multiple administrations. The virus may be administered at dosage of $1 \times 10^5$ plaque forming units (PFU), $5 \times 10^5$ PFU, at least $1 \times 10^6$ PFU, $5 \times 10^6$ or about $5 \times 10^6$ PFU, $1 \times 10^7$, at least $1 \times 10^7$ PFU, $1 \times 10^8$ or about $1 \times 10^8$ PFU, at least $1 \times 10^8$ PFU, about or at least $5 \times 10^8$ PFU, $1 \times 10^9$ or at least $1 \times 10^9$ PFU, $5 \times 10^9$ or at least $5 \times 10^9$ PFU, $1 \times 10^{10}$ PFU or at least $1 \times 10^{10}$ PFU, $5 \times 10^{10}$ or at least $5 \times 10^{10}$ PFU, $1 \times 10^{11}$ or at least $1 \times 10^{11}$, $1 \times 10^{12}$ or at least $1 \times 10^{12}$, $1 \times 10^{13}$ or at least $1 \times 10^{13}$. For example, the virus may be administered at a dosage of between about $10^7$-$10^{13}$, between about $10^8$-$10^{13}$, between about $10^9$-$10^{12}$, or between about $10^8$-$10^{12}$.

Adenoviruses according to the invention may be administered locally or systemically. For example, without limitation, oncolytic viruses according to the invention can be administered intravascularly (intraarterially or intravenously), intratumorally, intramuscularly, intradermally, intraperitoneally, subcutaneously, orally, parenterally, intranasally, intratracheally, percutaneously, intraspinally, ocularly, or intracranially.

Adenoviruses according to the invention may also be administered in a cellular carrier. In this respect, neuronal and mesenchymal stem cells have high migratory potential yet remain confined to tumor tissue. A subpopulation of adult mesenchymal cells (bone marrow derived tumor infiltrating cells or BM-TICs) has been shown, following injection into gliomas, to infiltrate the entire tumor. Thus, oncolytic viruses according to the invention can be administered in a virus-producing neuronal or mesenchymal stem cell (e.g. BM-TIC) carrier (e.g. by injection of the carrier cell into the tumor)

The quantity to be administered, both according to number of treatments and dose, depends on the subject to be treated, the state of the subject and the protection desired. Precise amounts of the therapeutic composition also depend on the judgment of the practitioner and are peculiar to each individual.

A gene encoding one or more co-stimulation/accessory molecules and/or genes encoding a cytokine may also be incorporated in the adenovirus genome or formulated with an adenovirus for use in the method of the present invention. Examples of costimulation molecules include but are not limited to B7-1, B7-2, ICAM1, ICAM-2, LFA-1, LFA-3, CD72 and the like. Examples of cytokines encompassed by the present invention include but are not limited to IL-2, IL-1, IL-3 through IL-9, IL-11, IL-13 through IL-15, G-CSF, M-CSF, GM-CSF, TNFα, IFNα, IFNγ, IL-10, IL-12, regulated upon activation, normal T expressed and presumably secreted cytokine (RANTES), and the like. Examples of chemokines encompassed by the present invention include but are not limited to CTAP III, ENA-78, GRO, I-309, PF-4, IP-10, LD-78, MBSA, MIP-1α, MIP1B and the like.

The invention claimed is:

1. A recombinant replication competent oncolytic adenovirus having a genome comprising one or more heterologous nucleic acid sequences encoding a tumor antigen or immunogenic peptide thereof, whereby the adenovirus expresses the tumor antigen(s) on its surface, wherein the one or more heterologous nucleic acid sequences are inserted in the hyper-variable region 5 of the hexon gene, into the H1 loop region, or into an E3 deleted gene region of the recombinant oncolytic adenovirus.

2. The recombinant replication competent oncolytic adenovirus of claim 1, wherein said recombinant oncolytic adenovirus comprises between 1 and 5 heterologous nucleic acid sequences each encoding a tumor antigen selected from the group consisting of MAGE-1, MAGE-2, MAGE-3, CEA, Tyrosinase, midkin, BAGE, CASP-8, β-catenin, CA-125, CDK-1, ESO-1, gp75, gp100, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY- ESO-1, C9orf112, SART1, SART2, SART3, BRAP, RTN4, GLEA2, TNKS2, KIAA0376, ING4, HSPH1, C13orf24, RBPSUH, C6orf153, NKTR, NSEP1, U2AF1L, CYNL2, TPR, SOX2, GOLGA, BMI1, COX-2, EGFRvIII, EZH2, LICAM, Livin, Livinβ, MRP-3, Nestin, OLIG2, ART1, ART4, B-cyclin, Gli1, Cav-1, cathepsin B, CD74, E-cadherin, EphA2/Eck, Fra-1/Fos1 1, GAGE-1, Ganglioside/GD2, GnT-V, β1,6-N, Ki67, Ku70/80, PROX1, PSCA, SOX10, SOX11, Survivin, UPAR and WT-1 or an immunogenic peptide thereof, whereby the recombinant oncolytic adenovirus expresses between 1 and 5 tumor antigens on its surface.

3. The recombinant replication competent oncolytic adenovirus of claim 1, wherein said recombinant oncolytic adenovirus comprises a heterologous nucleic acid encoding CEA or an immunogenic peptide thereof, whereby the recombinant oncolytic adenovirus expresses a chimeric surface protein comprising CEA or an immunogenic peptide thereof.

4. The recombinant replication competent oncolytic adenovirus of claim 3, wherein an immunogenic peptide from CEA comprising the amino acid sequence set forth in SEQ ID NO: 1.

5. The recombinant replication competent oncolytic adenovirus of claim 3, wherein the heterologous nucleic acid is inserted in hyper-variable region 5 of the hexon gene of the recombinant oncolytic adenovirus.

6. The recombinant replication competent oncolytic adenovirus of claim 1, wherein the recombinant oncolytic adenovirus comprises a heterologous nucleic acid sequence encoding EGFRvIII or an immunogenic peptide thereof, whereby the recombinant oncolytic adenovirus expresses a chimeric surface protein comprising EGFRvIII or an immunogenic peptide thereof.

7. The recombinant replication competent oncolytic adenovirus of claim 6, wherein the heterologous nucleic acid sequence is inserted into the H1 loop region of the adenovirus fiber gene.

8. The recombinant replication competent oncolytic adenovirus of claim 1, having a genome comprising 2-5 heterologous nucleic acid sequences each encoding a tumor antigen, whereby the recombinant oncolytic adenovirus expresses the tumor antigens on its surface.

9. The recombinant replication competent oncolytic adenovirus of claim 1, wherein the recombinant oncolytic adenovirus comprises a heterologous nucleic acid sequence encoding MAGE or an immunogenic peptide thereof.

10. The recombinant replication competent oncolytic adenovirus of claim 9, wherein the recombinant oncolytic adenovirus comprises a deletion in part or all of the E3 gene region.

11. The recombinant replication competent oncolytic adenovirus of claim 10, wherein a heterologous nucleic acid sequence encoding MAGE or an immunogenic peptide thereof is inserted in the E3 deleted gene region of the recombinant oncolytic adenovirus, whereby the recombinant oncolytic adenovirus expresses MAGE or an immunogenic peptide thereof.

12. The recombinant replication competent oncolytic adenovirus of claim 1, wherein the recombinant oncolytic adenovirus comprises a heterologous nucleic acid sequence encoding NY-ESO-1 or an immunogenic peptide thereof, whereby the recombinant oncolytic adenovirus expresses a chimeric surface protein comprising NY-ESO-1 or an immunogenic peptide thereof.

13. The recombinant replication competent oncolytic adenovirus of claim 12, wherein said heterologous nucleic acid sequence is inserted in the hyper-variable region 5 of the hexon gene of the recombinant oncolytic adenovirus.

14. The recombinant replication competent oncolytic adenovirus of claim 1 having a deletion in part or all of the E3 gene region and having a genome comprising:
   a) heterologous nucleic acid sequence encoding CEA or an immunogenic peptide thereof inserted into hyper-variable region 5 of the hexon gene of the recombinant oncolytic adenovirus;
   b) heterologous nucleic acid sequence encoding EGFRvIII or an immunogenic peptide thereof inserted into the H1 loop region of the fiber gene of the recombinant oncolytic adenovirus;
   c) heterologous nucleic acid sequence encoding MAGE or an immunogenic peptide thereof inserted in the E3 deleted gene region of the recombinant oncolytic adenovirus; and
   d) heterologous nucleic acid sequence encoding NY-ESO-1 or an immunogenic peptide thereof inserted in the hyper-variable region 5 of the hexon gene of the recombinant oncolytic adenovirus.

15. The recombinant replication competent oncolytic adenovirus of claim 1, wherein the recombinant oncolytic adenovirus is a human adenovirus type 5 or a hybrid comprising a human adenovirus type 5 component.

16. The recombinant replication competent oncolytic adenovirus of claim 15, wherein the recombinant oncolytic adenovirus is Delta-24 or Delta-24-RGD.

17. The recombinant replication competent oncolytic adenovirus of claim 1, wherein the adenovirus is selected from ICOVIR-5, ICOVIR-7, ONYX-015, ColoAd1, H101 and AD5/3-D24-GMCSF.

* * * * *

SEQUENCE LISTING

```
<160> NUMBER OF SEQ ID NOS: 7

<210> SEQ ID NO 1
<211> LENGTH: 23
<212> TYPE: PRT
<213> ORGANISM: Homo sapiens
<300> PUBLICATION INFORMATION:
<301> AUTHORS: Schrewe,H., Thompson,J., Bona,M., Hefta,L.J., Maruya,A.,
<302> TITLE: Cloning of the complete gene for carcinoembryonic antigen:
      analysis
<303> JOURNAL: Mol. Cell. Biol.
<304> VOLUME: 10
<305> ISSUE: 6
<306> PAGES: 2738-48
<307> DATE: 1990-06-01
<308> DATABASE ACCESSION NUMBER: GenBank/AAA62835
<309> DATABASE ENTRY DATE: 1995-03-06
<313> RELEVANT RESIDUES IN SEQ ID NO: (80)..(102)
```

-continued

```
<400> SEQUENCE: 1

Ile Ile Gly Tyr Val Ile Gly Thr Gln Gln Ala Thr Pro Gly Pro Ala
1               5                   10                  15

Tyr Ser Gly Arg Glu Ile Ile
            20

<210> SEQ ID NO 2
<211> LENGTH: 8
<212> TYPE: PRT
<213> ORGANISM: Artificial sequence
<220> FEATURE:
<223> OTHER INFORMATION: Synthetic EGFRvIII epitope
<300> PUBLICATION INFORMATION:
<302> TITLE: STRUCTURAL ALTERATIONS OF THE EGF RECEPTOR GENES IN HUMAN
      TUMORS
<308> DATABASE ACCESSION NUMBER: USPTO/US 6,455,498
<309> DATABASE ENTRY DATE: 2007-10-22
<310> PATENT DOCUMENT NUMBER: 09/664,752
<311> PATENT FILING DATE: 2000-09-19
<312> PUBLICATION DATE: 2002-09-24
<313> RELEVANT RESIDUES IN SEQ ID NO: (3)..(10)

<400> SEQUENCE: 2

Glu Lys Lys Gly Asn Tyr Val Val
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic EGFRvIII epitope
<300> PUBLICATION INFORMATION:
<302> TITLE: STRUCTURAL ALTERATIONS OF THE EGF RECEPTOR GENES IN HUMAN
      TUMORS
<308> DATABASE ACCESSION NUMBER: USPTO/US 6,455,498
<309> DATABASE ENTRY DATE: 2007-10-22
<310> PATENT DOCUMENT NUMBER: 09/664,752
<311> PATENT FILING DATE: 2000-09-19
<312> PUBLICATION DATE: 2002-09-24
<313> RELEVANT RESIDUES IN SEQ ID NO: (2)..(9)

<400> SEQUENCE: 3

Leu Glu Glu Lys Lys Gly Asn Tyr
1               5

<210> SEQ ID NO 4
<211> LENGTH: 11
<212> TYPE: PRT
<213> ORGANISM: Artificial sequence
<220> FEATURE:
<223> OTHER INFORMATION: Synthetic EGFRvIII epitope
<300> PUBLICATION INFORMATION:
<302> TITLE: STRUCTURAL ALTERATIONS OF THE EGF RECEPTOR GENES IN HUMAN
      TUMORS
<308> DATABASE ACCESSION NUMBER: USPTO/US 6,455,498
<309> DATABASE ENTRY DATE: 2007-10-22
<310> PATENT DOCUMENT NUMBER: 09/664,752
<311> PATENT FILING DATE: 2000-09-19
<312> PUBLICATION DATE: 2002-09-24
<313> RELEVANT RESIDUES IN SEQ ID NO: (2)..(12)

<400> SEQUENCE: 4

Leu Glu Glu Lys Lys Gly Asn Tyr Val Val Thr
1               5                   10

<210> SEQ ID NO 5
<211> LENGTH: 13
<212> TYPE: PRT
```

```
<213> ORGANISM: Artificial sequence
<220> FEATURE:
<223> OTHER INFORMATION: Synthetic EGFRvIII epitope
<300> PUBLICATION INFORMATION:
<302> TITLE: STRUCTURAL ALTERATIONS OF THE EGF RECEPTOR GENES IN HUMAN
      TUMORS
<308> DATABASE ACCESSION NUMBER: USPTO/US 6,455,498
<309> DATABASE ENTRY DATE: 2007-10-22
<310> PATENT DOCUMENT NUMBER: 09/664,752
<311> PATENT FILING DATE: 2000-09-19
<312> PUBLICATION DATE: 2002-09-24
<313> RELEVANT RESIDUES IN SEQ ID NO: (2)..(14)

<400> SEQUENCE: 5

Leu Glu Glu Lys Lys Gly Asn Tyr Val Val Thr Asp His
1               5                   10

<210> SEQ ID NO 6
<211> LENGTH: 14
<212> TYPE: PRT
<213> ORGANISM: Artificial sequence
<220> FEATURE:
<223> OTHER INFORMATION: Synthetic EGFRvIII epitope
<300> PUBLICATION INFORMATION:
<302> TITLE: STRUCTURAL ALTERATIONS OF THE EGF RECEPTOR GENES IN HUMAN
      TUMORS
<308> DATABASE ACCESSION NUMBER: USPTO/US 6,455,498
<309> DATABASE ENTRY DATE: 2007-10-22
<310> PATENT DOCUMENT NUMBER: 09/664,752
<311> PATENT FILING DATE: 2000-09-19
<312> PUBLICATION DATE: 2002-09-24
<313> RELEVANT RESIDUES IN SEQ ID NO: (2)..(15)

<400> SEQUENCE: 6

Leu Glu Glu Lys Lys Gly Asn Tyr Val Val Thr Asp His Cys
1               5                   10

<210> SEQ ID NO 7
<211> LENGTH: 14
<212> TYPE: PRT
<213> ORGANISM: Homo sapiens
<300> PUBLICATION INFORMATION:
<301> AUTHORS: Chen,Y.T., Scanlan,M.J., Sahin,U., Tureci,O., Gure,A.O.,
      Tsang,S.,
<302> TITLE: A testicular antigen aberrantly expressed in human cancers
      detected
<303> JOURNAL: Proc. Natl. Acad. Sci. U.S.A.
<304> VOLUME: 94
<305> ISSUE: 5
<306> PAGES: 1914-8
<307> DATE: 1997-03-04
<308> DATABASE ACCESSION NUMBER: GenBank/U87459
<309> DATABASE ENTRY DATE: 1997-01-28
<313> RELEVANT RESIDUES IN SEQ ID NO: (157)..(170)
<300> PUBLICATION INFORMATION:
<308> DATABASE ACCESSION NUMBER: GenBank: AAB49693
<309> DATABASE ENTRY DATE: 1997-01-28
<313> RELEVANT RESIDUES IN SEQ ID NO: (157)..(170)

<400> SEQUENCE: 7

Ser Leu Leu Met Trp Ile Thr Gln Cys Phe Leu Pro Val Phe
1               5                   10
```